(12) United States Patent
Townsend et al.

(10) Patent No.: US 6,270,468 B1
(45) Date of Patent: Aug. 7, 2001

(54) SHOE, ANKLE ORTHOSIS AND METHOD FOR PROTECTING THE ANKLE

(76) Inventors: Barry W. Townsend, 400 Houchin Rd., Bakersfield, CA (US) 93304; Henry E. Pfister, 8817 Timerloch Ct., Bakersfield, CA (US) 93304

(*) Notice: Subject to any disclaimer, the term of this patent is extended or adjusted under 35 U.S.C. 154(b) by 0 days.

(21) Appl. No.: 09/606,076

(22) Filed: Jun. 29, 2000

Related U.S. Application Data

(62) Division of application No. 08/896,457, filed on Jul. 18, 1997.

(51) Int. Cl.⁷ .................................. A61F 5/00; A43B 5/00
(52) U.S. Cl. .................................. 602/27; 602/65; 36/114
(58) Field of Search .................................. 36/1, 5, 83, 88, 36/89, 90, 91, 92, 114, 116, 118, 119, 7.8, 7.1 A, 27, 140, 142, 143, 144, 145, 172, 173; D2/314, 310, 309, 311; 602/23, 24, 27, 29, 60, 62, 65, 66

(56) References Cited

U.S. PATENT DOCUMENTS

| | | | |
|---|---|---|---|
| D. 295,229 | * | 4/1988 | Brown et al. .......................... D2/314 |
| D. 300,282 | * | 3/1989 | Brown et al. .......................... D2/314 |
| 2,156,086 | | 4/1939 | Hack et al. . |
| 2,261,453 | | 11/1941 | Reinhart et al. . |
| 2,972,822 | | 2/1961 | Tanner . |
| 3,466,763 | | 9/1969 | Levin . |
| 4,183,156 | | 1/1980 | Rudy . |
| 4,219,945 | | 9/1980 | Rudy . |
| 4,340,626 | | 7/1982 | Rudy . |
| 4,411,077 | * | 10/1983 | Slavitt .......................... 36/89 |
| 4,441,265 | | 4/1984 | Burns et al. . |
| 4,451,996 | * | 6/1984 | Norton et al. .......................... 36/129 |
| 4,489,719 | | 12/1984 | Lapenski . |
| 4,523,394 | | 6/1985 | Linh et al. . |
| 4,547,981 | | 10/1985 | Thais et al. . |
| 4,554,912 | | 11/1985 | Haberman . |
| 4,577,419 | | 3/1986 | Chassaing . |
| 4,621,648 | | 11/1986 | Ivany . |

(List continued on next page.)

OTHER PUBLICATIONS

Smith & Nephew Don Joy ALP PLUS (Ankle Ligament Protector), Rev. 0495, 1 page.
Wernich et al., *Lower Extremity Function and Normal Mechanics*, textbook, pp. 1–31, 34–57.
"Orthopedics, Ankle/Foot Orthoses", pp. 363–364.
*Foot Splints, AFO*, pp. D84–D87.

*Primary Examiner*—Kim M. Lewis
(74) *Attorney, Agent, or Firm*—Antonelli, Terry, Stout & Kraus, LLP

(57) ABSTRACT

An improved athletic shoe, ankle orthosis and method for protecting the ankle against injury, limit subtalar joint motion of the ankle by controlling the motions of segments of the subtalar joint fore and aft of the subtalar joint while permitting motion of the foot about the ankle joint. A supporting structure a part of or connected to the shoe or orthosis is preferably in the form of a heel-sole counter provided about the heel and at least a portion of the foot forward of the subtalar joint. The supporting structure has a semi-rigid shape retaining character which is not collapsible vertically and which together with the shoe or orthosis limits torsional movement of the foot about the longitudinal axis of the subtalar joint as seen in a top plan view thereof by an upwardly extending portion thereof which acts as a torsion bar that is, in turn, secured to the lower leg. Preferably, the torsion bar has directional properties for resisting bending which are most rigid in a direction orthogonal or nearly orthogonal to the longitudinal axis of the subtalar joint. In a disclosed embodiment of the shoe motion of the midtarsal joint is also limited by the supporting structure to aid in limiting subtalar joint motion and shoe rollover. The shoe is secured to the foot by way of a strap arrangement which applies a force to the foot in a direction which, together with the heel-sole counter opposes the subtalar joint motion in supination.

16 Claims, 20 Drawing Sheets

U.S. PATENT DOCUMENTS

| | | |
|---|---|---|
| 4,649,939 | 3/1987 | Curtis . |
| 4,766,681 * | 8/1988 | O'Rourke et al. .......... 36/89 |
| 4,821,430 | 4/1989 | Flemming et al. . |
| 4,864,741 * | 9/1989 | Beauchemin .............. 36/89 |
| 4,906,502 | 3/1990 | Rudy . |
| 4,922,630 | 5/1990 | Robinson . |
| 4,938,777 | 7/1990 | Mason et al. . |
| 5,083,361 | 1/1992 | Rudy . |
| 5,109,613 | 5/1992 | Van Dyke . |
| 5,203,793 | 4/1993 | Lyden . |
| 5,323,549 | 6/1994 | Segel et al. . |
| 5,353,459 | 10/1994 | Potter et al. . |
| 5,379,530 | 1/1995 | Bell et al. . |
| 5,392,535 | 2/1995 | Van Noy et al. . |
| 5,396,675 | 3/1995 | Vincent et al. . |
| 5,475,935 | 12/1995 | Frost . |
| 5,771,609 | 6/1998 | Messmer . |
| 5,810,754 | 9/1998 | Kenosh . |
| 5,894,684 | 4/1999 | Sand et al. . |

* cited by examiner

DORSAL BORDER OF CALCANEUS

CALCANEAN PROCESS OF CUBOID

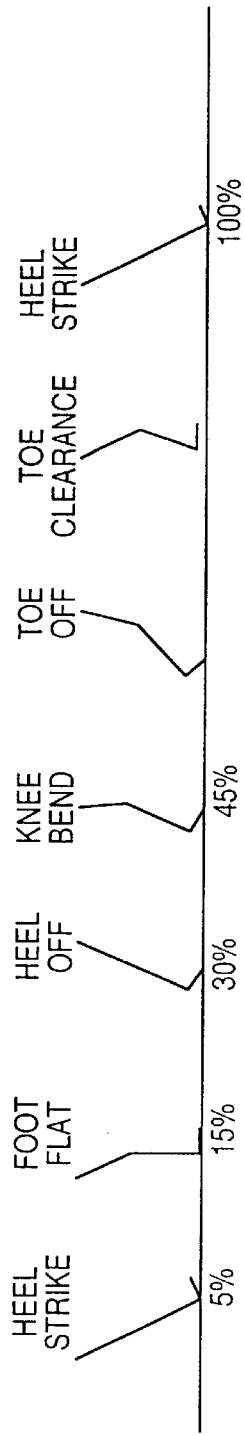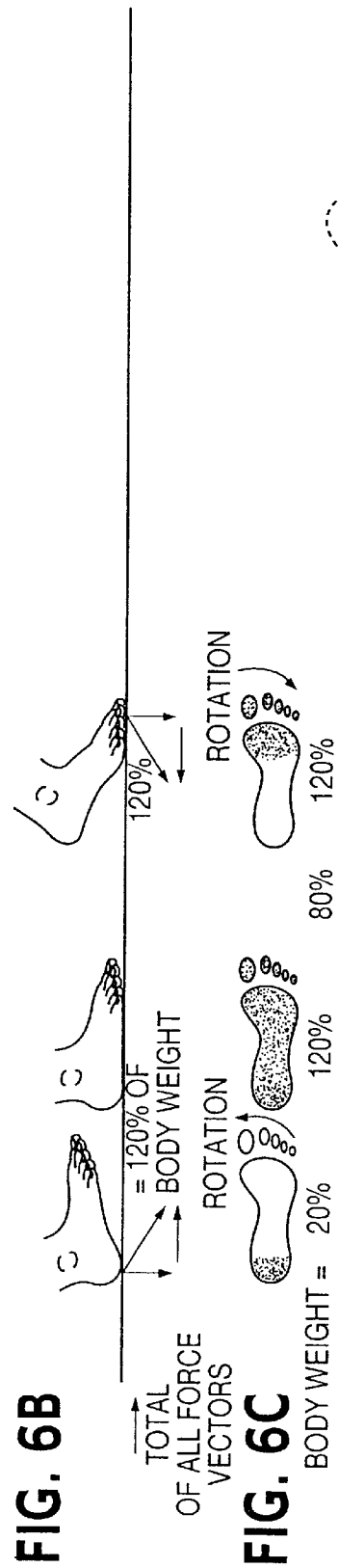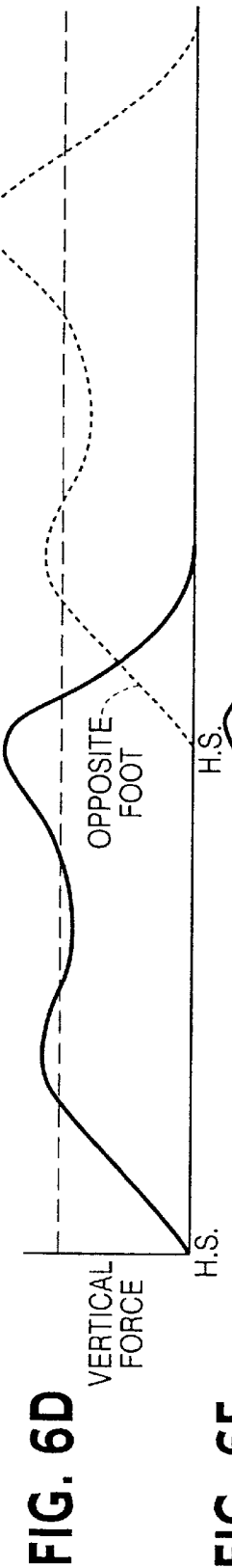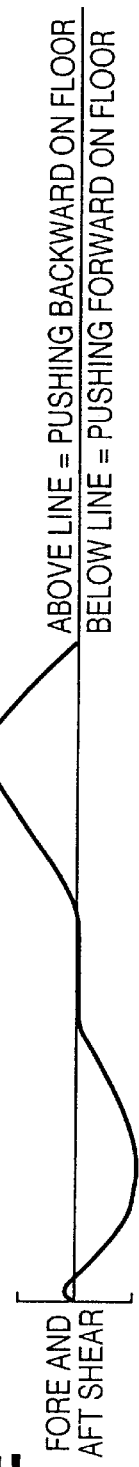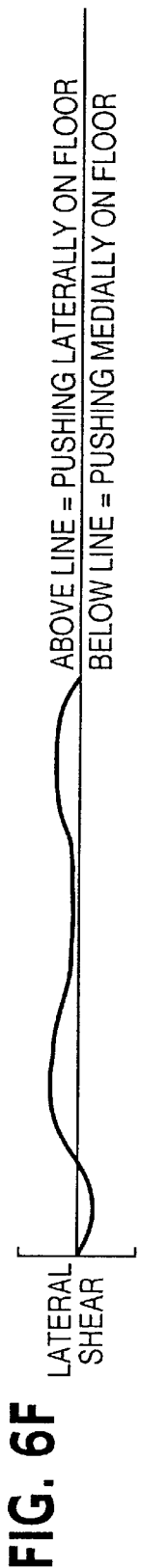

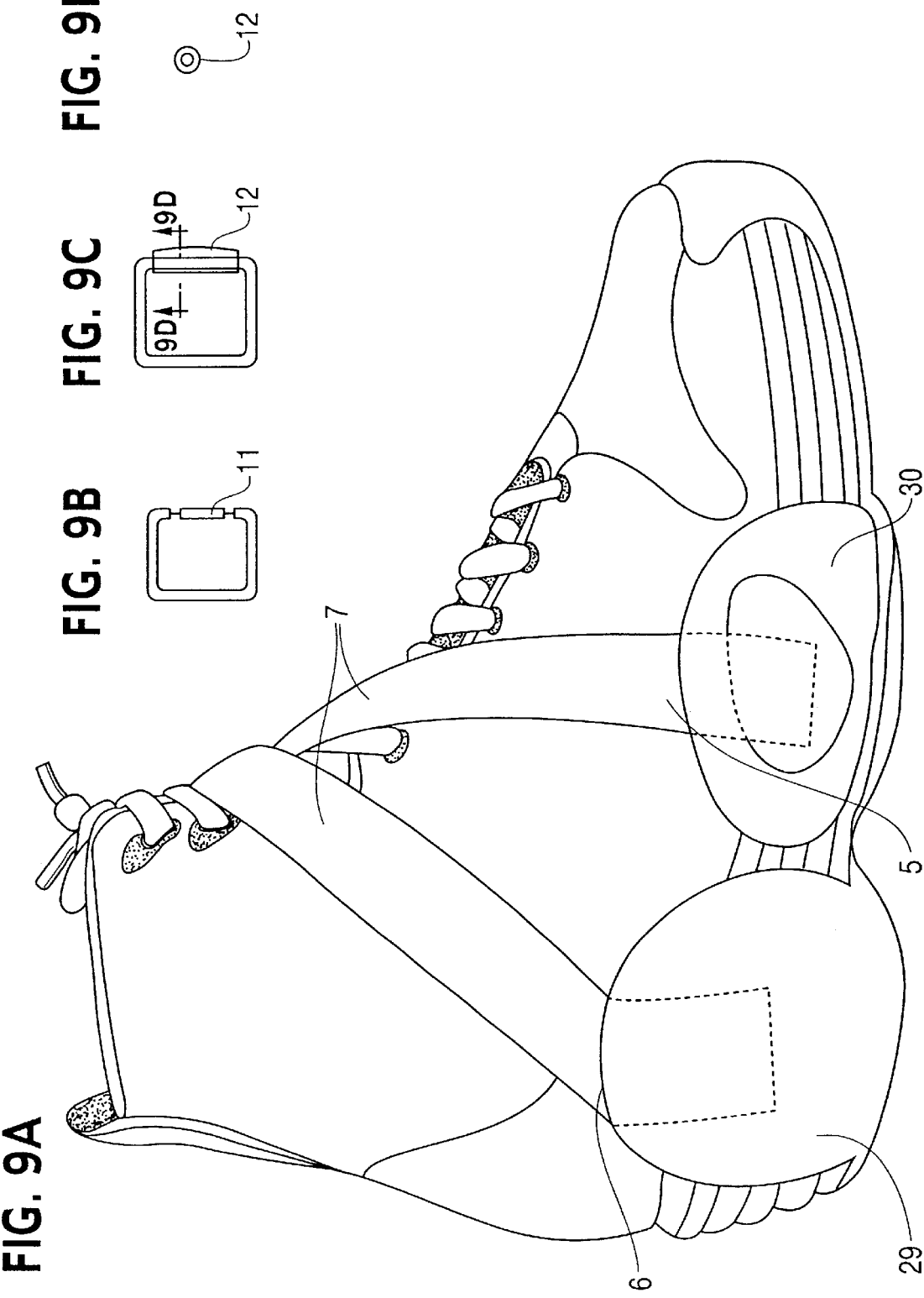
FIG. 9A
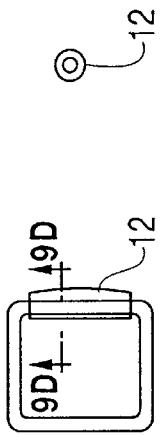
FIG. 9B
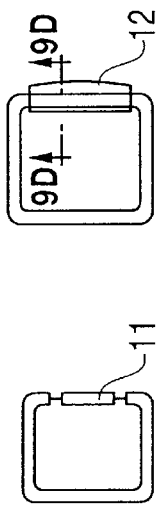
FIG. 9C
FIG. 9D

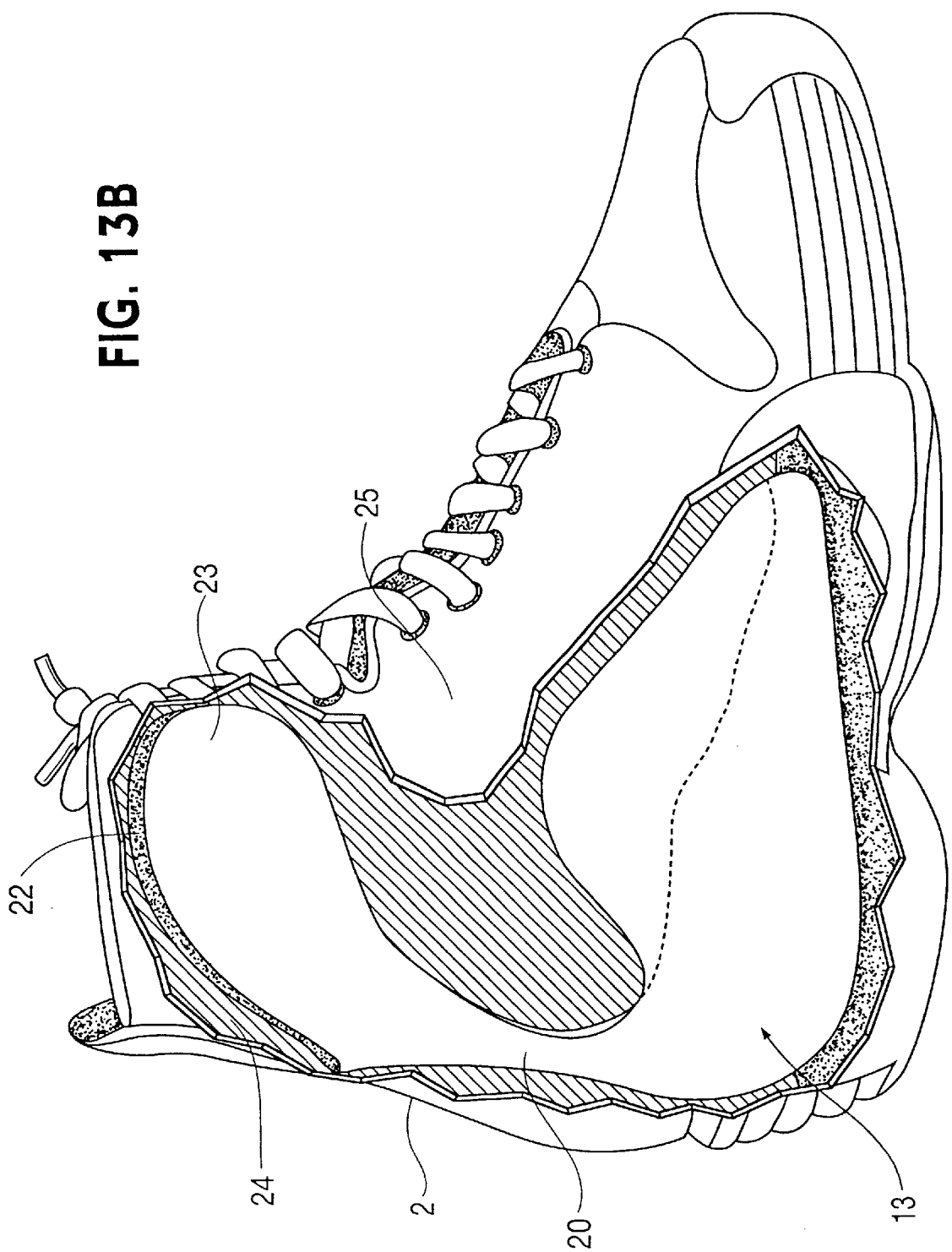

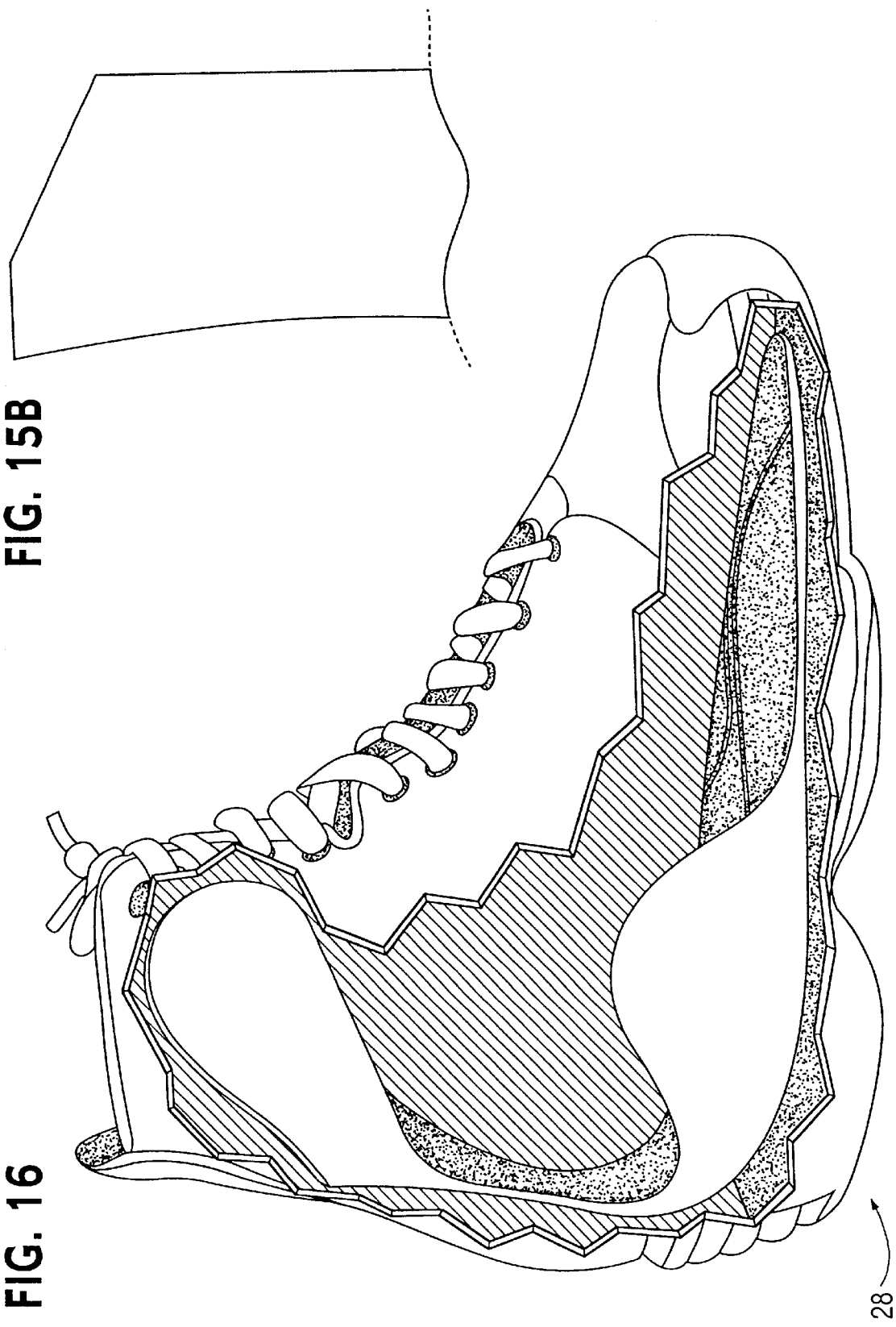

SHOE, ANKLE ORTHOSIS AND METHOD FOR PROTECTING THE ANKLE

CROSS-REFERENCE TO RELATED APPLICATION

This application is a divisional of U.S. application Ser. No. 08/896,457, filed Jul. 18, 1997.

FIELD OF THE INVENTION

The present invention relates to an improved shoe, ankle orthosis and method for protecting the ankle. More specifically, an athletic shoe, particularly a high-top tennis shoe, is disclosed which eliminates or reduces shoe rollover and inversion ankle injury while not restricting normal motion of the foot during gait, running and jumping.

BACKGROUND AND SUMMARY OF INVENTION

Inversion and eversion ankle injuries are common in all athletic endeavors. Eversion ankle joint injuries account for ten percent (10%) of ankle injuries and inversion ankle injuries occur ninety percent (90%) of the time. These injuries are a result of the ankle joint or subtalar joint being forced beyond their normal ranges (arcs) of motion causing a tearing or stretching of the lateral collateral talo fibular and/or calcaneo-fibular ligaments. In extreme cases of force and trauma, avulsion of the lateral malleolus and oblique or vertical fractures of the medial malleolus may result. These injuries may happen from the athlete stopping abruptly while cutting laterally, or by his/her stepping with the medial side of the foot on a player's foot or ball. Once these ligaments have been stretched these injuries can and do become chronic in nature.

Present ankle orthoses and shoes or both in conjunction have not proven to be effective in preventing or treating these injuries while at the same time not unduly restricting normal motions of the athlete's foot. Acceptable treatment methods and ankle orthosis designs include taping, lace up ankle supports with steel or plastic stays, or "figure eight" straps, air casts which are medial and lateral support structures hinged at the ankle or not, and heel wedges. These known attempts are not completely satisfactory in that they unduly limit normal motion of the foot and/or are not highly effective in preventing or treating these injuries. There is a need for an improved shoe, ankle orthosis and method for protecting the ankle which overcome the drawbacks and limitations of the prior art to prevent or treat these injuries while allowing normal motion of the foot.

The efficiency of treatment utilizing known orthoses and shoes is hindered by the fact that the shoes and braces are not attached to one another and the foot can slip or slide to the lateral side of the shoe's foot bed and in extreme cases can slide off the entire foot bed. The sole can turn over (medial side raises while lateral side is weight bearing). This lateral movement of the foot and lack of lateral support from the shoe causes the sole of the shoe to move medially in relationship to the foot. This medial migration (movement) of the shoe sole causes the weight line of the shoe to shift medial of the ankle joint or subtalar joint's axis of rotation. The movement creates uncontrollable and unacceptable inversion torque which causes inversion injuries to the ankle. Another problem with present shoe and orthosis designs is that the tensioning of vertically positioned straps collapses circumferential ankle straps which slide down the ankle in time. As a result, the vertically positioned straps lose their ability to support the lateral structures of the ankle.

An object of the present invention is to provide an improved shoe, orthosis and method for protecting the ankle which avoid the aforementioned drawbacks and limitations of conventional shoes, orthoses and methods. More particularly, an object of the invention is to provide an improved athletic shoe, orthosis and method for protecting the ankle which on one hand will not impede normal ranges of motion in the ankle and subtalar joints which are necessary to walk, run or jump, while on the other hand will protect the ankle against injury.

These and other objects are attained by the improved shoe of the present invention which comprises a mid- or high-top upper, a heel-sole and means for securing the shoe on a person's foot, and wherein a heel-sole counter is provided. The heel-sole counter has a semi-rigid, shape-retaining character and includes a first portion adapted to be secured about the lower leg, a second portion spaced from the first portion and adapted to be secured about the heel and at least a portion of the foot forward of the subtalar joint for limiting subtalar joint motion by controlling the motions of segments of the subtalar joint fore and aft of the subtalar joint while permitting motion of the foot about the ankle joint, and an upwardly extending portion extending between the first and second portions for limiting torsional movement of the second portion about a longitudinal axis of the subtalar joint, as seen in a top plan view thereof, when the shoe is secured on the foot. In a disclosed embodiment, the heel-sole counter and shoe limit motion of the subtalar joint to within a normal range of motion of the subtalar joint. More specifically, supination of the subtalar joint beyond this normal range is prevented to eliminate or reduce inversion ankle injury.

For this purpose, the upwardly extending portion of the heel-sole counter of a disclosed embodiment includes a torsion bar which, as seen in transverse plan view thereof adjacent the second portion of the heel-sole counter, is elongated and relatively rigid against bending in a direction orthogonal or nearly orthogonal to the longitudinal axis of the subtalar joint as seen in a top plan view thereof while the torsion bar is narrower and more flexible in bending in another direction transverse to the direction of elongation. A further feature of the disclosed embodiment is that the torsion bar is progressively twisted along its length between the first and second portions of the heel-sole counter so that the aforementioned another direction is more forwardly facing adjacent the first portion to permit the foot to move about the ankle joint while effectively limiting motion of the second portion about the longitudinal axis of the subtalar joint.

The second portion of the heel-sole counter in the preferred embodiment extends forward of the subtalar joint on the lateral side of the foot to at least the cuboid tarsal of the foot and atop a lateral portion of the foot above the cuboid tarsal for limiting motion of the midtarsal joint and the subtalar joint of the foot. The means for securing is vertically supported by the heel-sole counter when the shoe is secured on the foot for avoiding collapse and loss of tension in the means for securing.

The first portion of the heel-sole counter is secured about the lower leg by the means for securing for yieldably resisting rotation of the tibia and fibula in a plane transverse to a longitudinal axis of the leg. The heel-sole counter in a disclosed embodiment has a construction which allows free dorsiflexion of the foot and plantarflexion with resistance. According to a further feature of the invention, the heel-sole counter in one form of the invention is configured to position the foot in the shoe in slight dorsiflexion such that when the foot plantarflexes it creates tension on the heel-sole counter for assisting the foot upon its return to its starting position.

The first portion, second portion and upwardly extending portion of the heel-sole counter are formed integrally with one another in one form of the invention. For example, the entire heel-sole counter can be formed of plastic by molding. In another form of the invention the heel-sole counter is formed of a plurality of segments such as a mid-sole member and a heel counter which are employed in combination in the shoe as the heel-sole counter.

The heel-sole counter is preferably formed integrally with a side wall of the upper and the heel-sole of the shoe during manufacture. Alternatively, the heel-sole counter can be a separate orthosis which is used inside of the shoe in combination with the shoe wherein means are provided for connecting the shoe and heel-sole counter to one another at least when secured on the foot.

A further embodiment of the shoe of the present invention employs a heel-sole counter which includes a sole extension in the shape of a single leaf spring which is capable of storing energy when deflected to provide assistance during the stance phase heel-off portion of gait, running and jumping activities for improving athletic performance. Where the heel-sole counter is integrated in the shoe, the sole extension is flattened in fabrication of the shoe to pre-load the spring.

The means for securing the shoe on a person's foot in the disclosed, preferred embodiment of the invention includes an external strap which is non-stretchable in length and which can be tensioned over the anterior aspect of the ankle between points of the shoe on or about the lateral heel-sole of the shoe and the medial anterior aspect of the ankle. The external strap is free floating intermediate its ends. Its two ends are connected to the shoe at respective points on or about the lateral heel-sole of the shoe fore and aft of the axis of the ankle joint as seen in a top plan view of the foot. The free floating intermediate portion of the strap is secured on the medial anterior aspect of the ankle by means of a free floating loop and a second adjustable strap connected thereto on the medial side of the shoe for adjustably tensioning the free floating strap. The use of this strap arrangement together with other features of the invention prevents shoe rollover.

An ankle orthosis according to the invention comprises a heel-sole counter having a semi-rigid, shape-retaining character and means for securing the heel-sole counter about the leg and foot of a user. As in the case with the aforementioned shoe of the present invention, the heel-sole counter preferably comprises a first portion adapted to be secured about the lower leg, a second portion spaced from the first portion and adapted to be secured about the heel and at least a portion of the foot forward of the subtalar joint for limiting subtalar joint motion by controlling the motion of segments of the subtalar joint fore and aft of the subtalar joint while permitting motion of the foot about the ankle joint. The first and second portions of the heel-sole counter of the orthosis are connected to one another in spaced relation by an upwardly extending portion of the heel-sole counter for securing the second portion against torsional movement about the longitudinal axis of the subtalar joint, as seen in a top plan view thereof, when the orthosis is secured on the foot and leg.

The upwardly extending portion of the heel-sole counter in a disclosed orthosis includes a torsion bar which in one form of the invention is asymmetrically positioned with respect to a longitudinal axis of the foot as seen in a top view thereof when the orthosis is in use such that torsional forces on the second portion of the heel-sole counter about the longitudinal axis of the subtalar joint, as seen in a top plan view thereof, are effectively resisted to prevent shoe rollover and inversion while the counter can flex to permit the foot to move about the ankle joint. The means for securing the heel-sole counter about the leg and foot of a user in a disclosed embodiment of the orthosis comprises two layers of material within which the heel-sole counter is sandwiched and means for securely connecting the layers and the heel-sole counter therebetween to one another and about the leg and foot of a user.

The method of protecting a person's ankle of the invention, as seen from the above description of the shoe and orthosis of the invention taken with the following detailed description of disclosed embodiments, comprises limiting subtalar joint motion of the ankle by controlling the motions of segments of the subtalar joint fore and aft of the subtalar joint while permitting motion of the foot about the ankle joint. The controlling includes providing a supporting structure about the heel and at least a portion of the foot forward of the subtalar joint for controlling the motions of segments of the subtalar joint fore and aft of the subtalar joint, and securing the supporting structure to limit torsional movement thereof about a longitudinal axis of the subtalar joint, as seen in a top plan view thereof, by an upwardly extending portion of the supporting structure secured to the lower leg. Preferably, the motion of the subtalar joint is limited by the controlling to within a normal range of motion of the subtalar joint, especially in supination of the subtalar joint. The motion of the subtalar joint is triplanar in nature and according to the invention this motion is limited in all three planes, that is, in the frontal, sagittal and transverse (cross-section of the foot) reference planes of the foot by the controlling according to the invention. The segments of the subtalar joint whose motion is controlled in closed chain subtalar joint movement during supination, for example, include limiting the inversion of the calcaneus aft of the subtalar joint and the abduction and dorsiflexion of the anterior aspect of the talus and the lateral shifting of the anterior aspect of the calcaneus fore of the subtalar joint. Preferably, this control is facilitated by also limiting the lateral shifting of the midtarsal joint at the cuboid tarsal of the foot which tends to occur in closed kinetic chain supination of the subtalar joint.

Further, according to the method of the invention, the upwardly extending portion of the supporting structure is secured to the lower leg in a manner to yieldably resist rotation of the tibia in a plane transverse to a longitudinal axis of the leg. Subtalar joint motion in the closed chain is linked with motions at other lower extremity joints including such rotation of the tibia. Relative external rotation of the tibia, for example, occurs with subtalar joint supination. Thus, control is enhanced according to the invention by employing the upwardly extending portion to both limit torsional movement of the supporting structure about a longitudinal axis of the subtalar joint, as seen in a top plan view thereof, for limiting motion of segments of the subtalar joint while yieldably resisting subtalar joint motion by way of providing resistance to the associated rotation of the tibia.

As explained more fully hereinafter, the subtalar joint either pronates or supinates about an oblique axis. The method of the invention further includes securing the supporting structure to the foot in a manner which applies a force to the foot in a direction which is orthogonal or nearly orthogonal to this oblique axis of the subtalar joint for effectively limiting motion thereof together with the supporting structure, especially in a direction to oppose supination of the subtalar joint in the preferred embodiments of the invention. The method of the invention can be performed with a shoe or an orthosis according to the invention, or with an orthosis of the invention in conjunction with a conventional shoe.

These and other objects, features and advantages of the present invention will become more apparent from a consideration of the following detailed description of disclosed embodiments of the invention and the accompanying drawings.

BRIEF DESCRIPTION OF DRAWINGS

FIGS. 6A–6F are respective diagrams showing forces and displacements of the foot associated with functioning of the subtalar and ankle joints during walking.

FIG. 9A is a lateral side view of the shoe of FIGS. 7 and 8.

FIGS. 9B and 9C are top plan views of respective loops for the external strap of the shoe of FIGS. 7–9A.

FIG. 9D is a cross section of a portion of the loop of FIG. 9C taken along the line I—I.

FIG. 13B is a lateral side view of the shoe of FIG. 13A but with a portion of the shoe cutaway to illustrate the short version heel-sole counter in the shoe.

FIG. 15B is a schematic, top plan view of the trim on the distal end of the leaf-spring extension of the counter of FIG. 15A.

FIG. 16 is a lateral side view like that of FIG. 13B, partially cutaway, showing the heel-sole counter of FIG. 15 integrated in the high top tennis shoe of the invention of FIG.

1 in place of the short version of FIGS. 13A–13D with the single leaf-spring extension of the counter being flattened to preload it in compression within the shoe.

Figure 17:
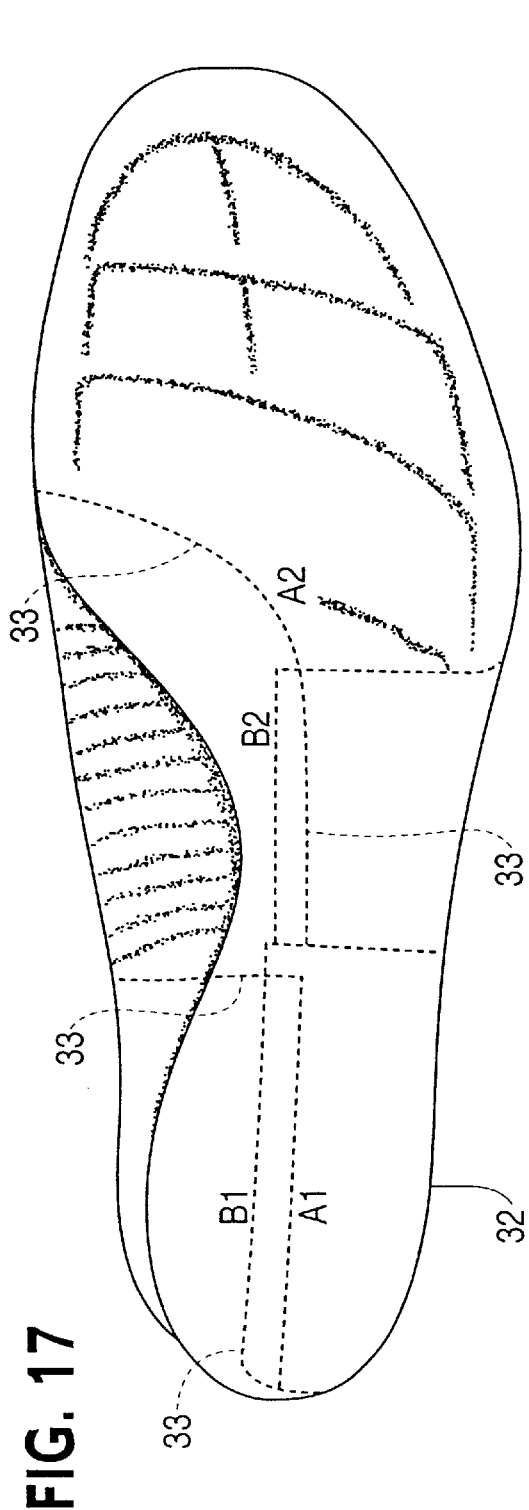

FIG. 17 is a plantar (bottom) view of the foot showing cut lines of arch supports which may be used in the shoe of the present invention, the cut lines for $A_1$, reflecting a medial heel wedge, $A_2$ a medial heel and sole wedge, $B_1$, a lateral heel wedge and $B_2$ a lateral heel and sole wedge.

Figure 18:

FIG. 18 is a side view of the medial aspect of arch supports $A_1$ and $A_2$ of FIG. 17.

Figure 7:
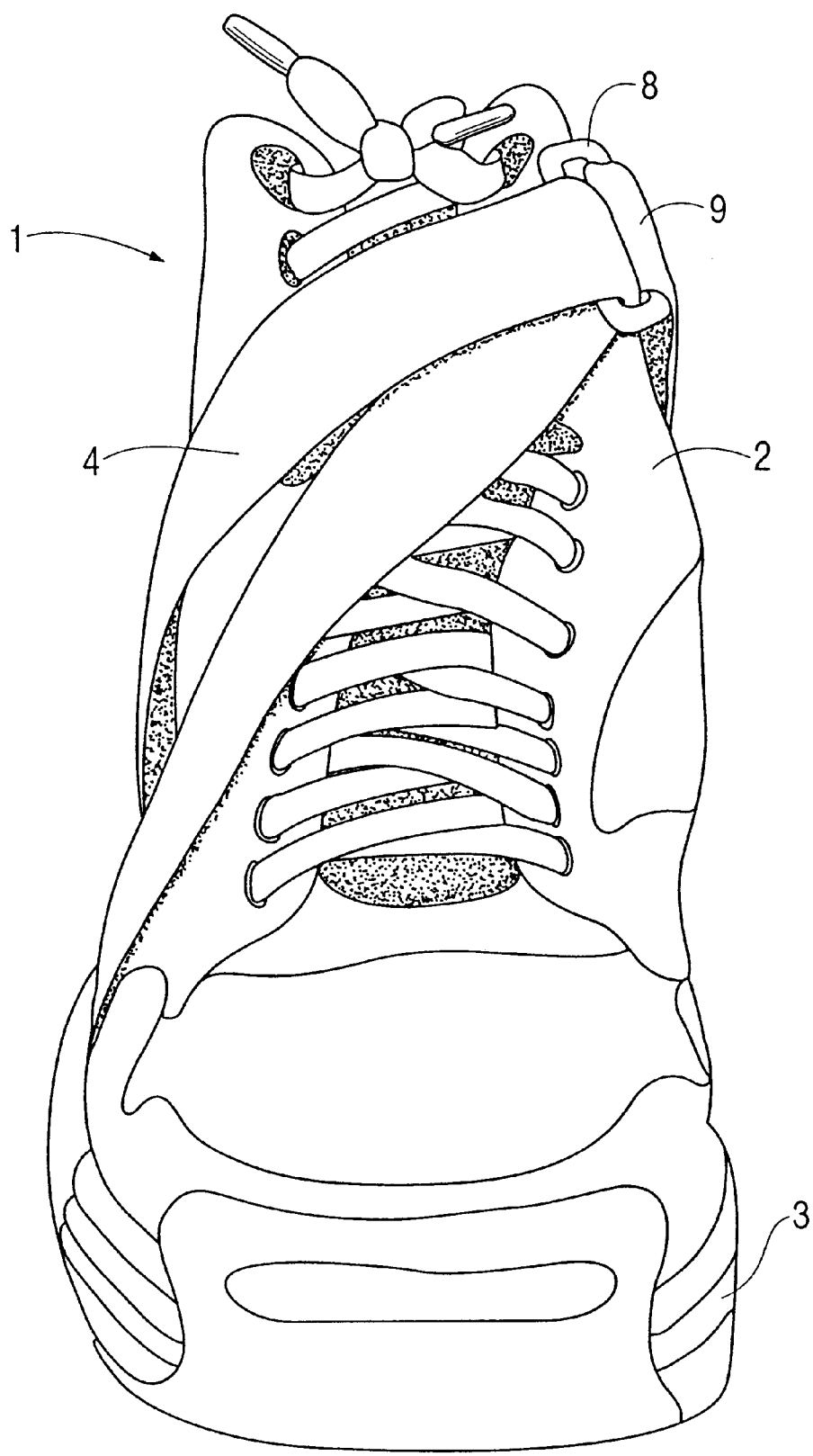
FIG. 7 is a front view of a preferred embodiment of a high-top tennis shoe for the right foot according to the present invention.
Figure 8:
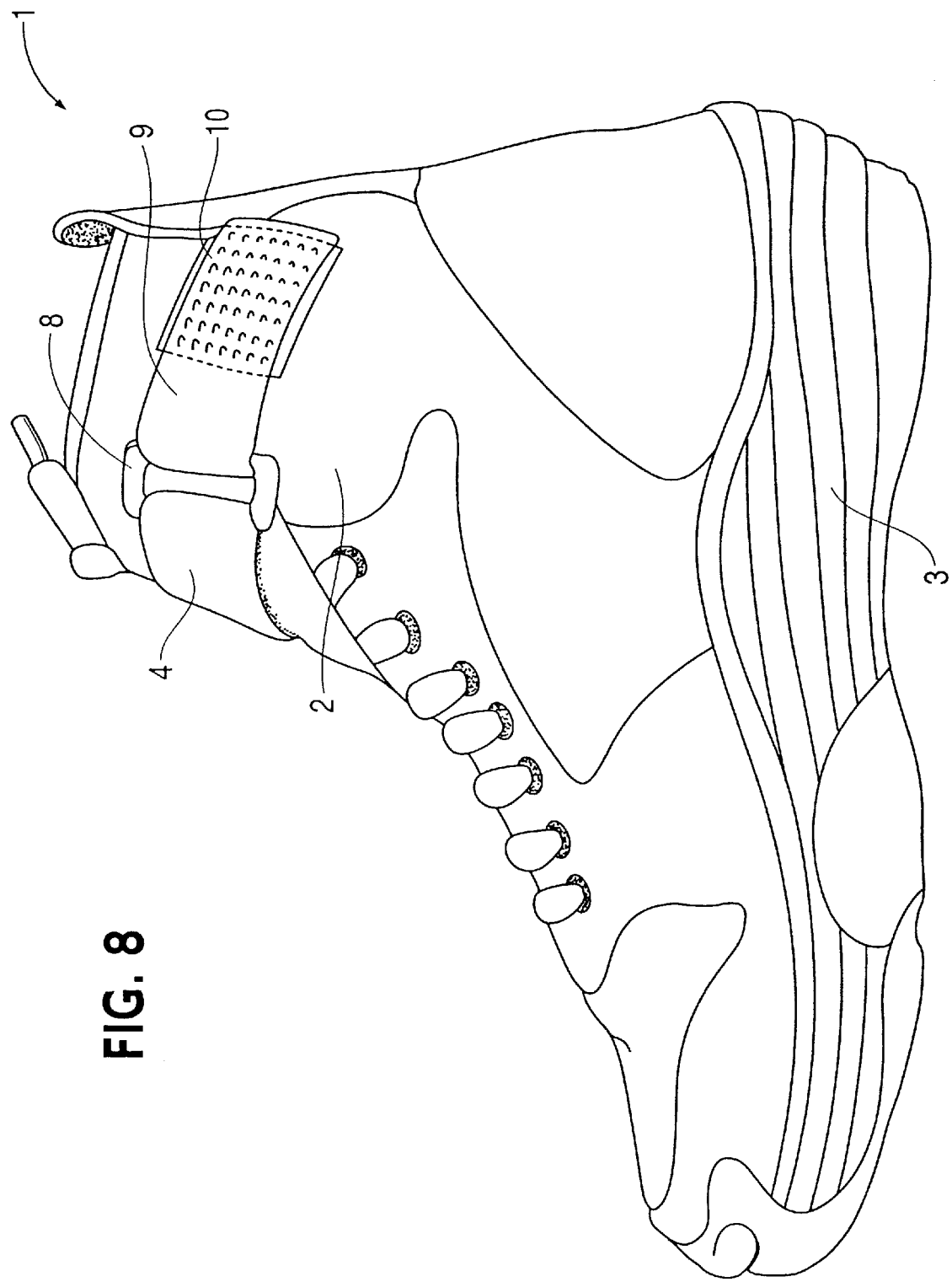
FIG. 8 is a medial side view of the shoe of FIG. 7.
Figure 10:
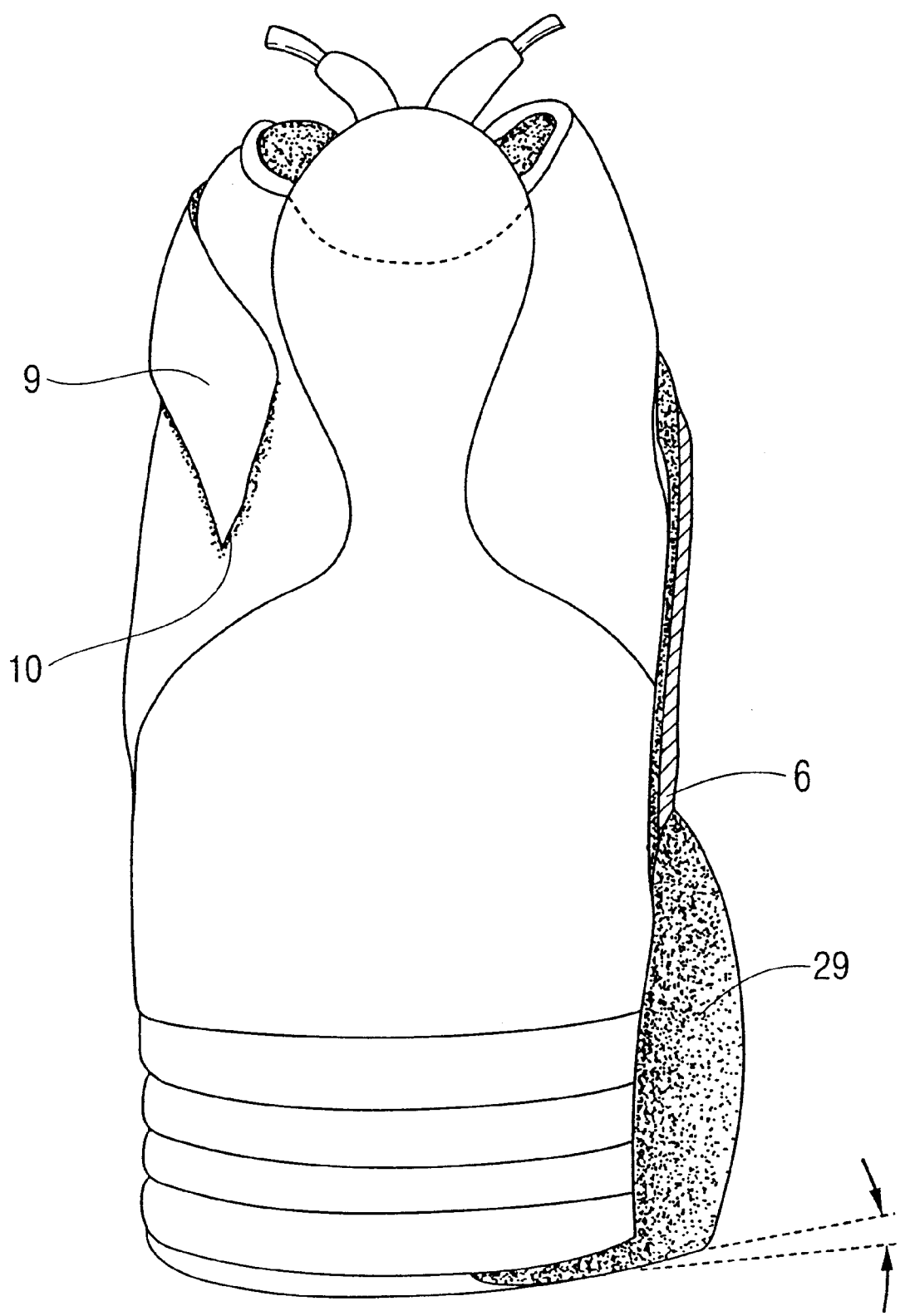
FIG. 10 is a posterior view of the shoe depicting a heel lateral wedge buttress which may be employed on the shoe in the vicinity of the heel.
Figure 11:
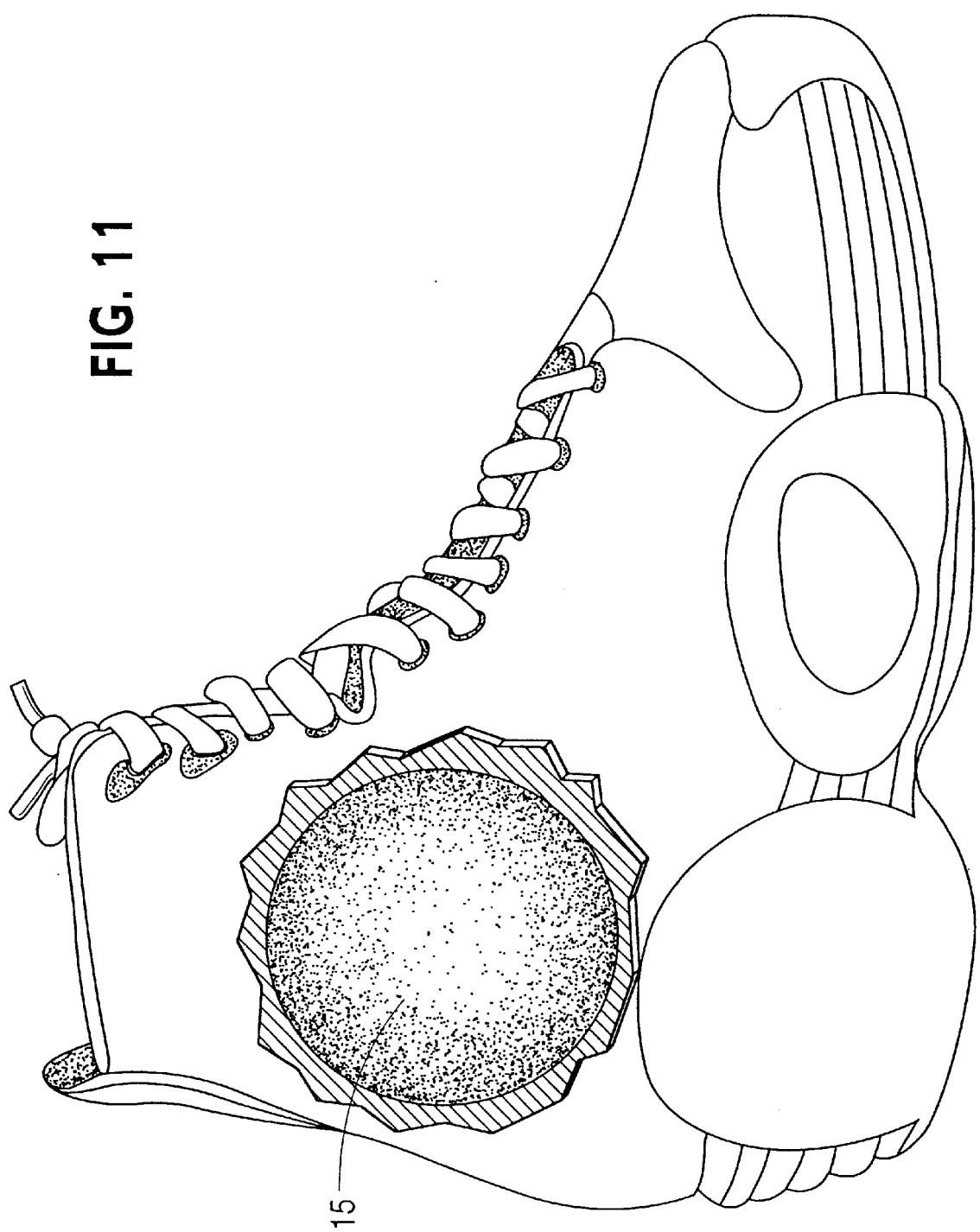
FIG. 11 is a lateral side view of the shoe similar to FIG. 9A but without the external straps being shown and with a portion of the sidewall of the shoe cutaway to depict a pad or air bladder of the shoe over the lateral malleolus.
Figure 19:
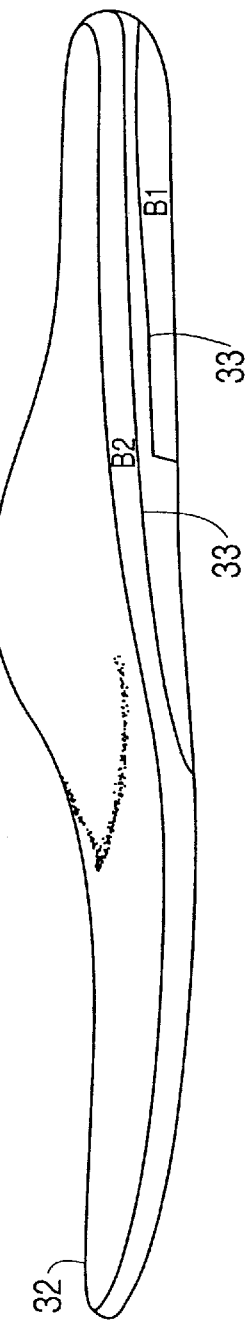

FIG. 19 is a side view of the arch supports $B_1$ and $B_2$ of FIG. 7 showing the lateral aspect of each of the supports.

Figure 20:
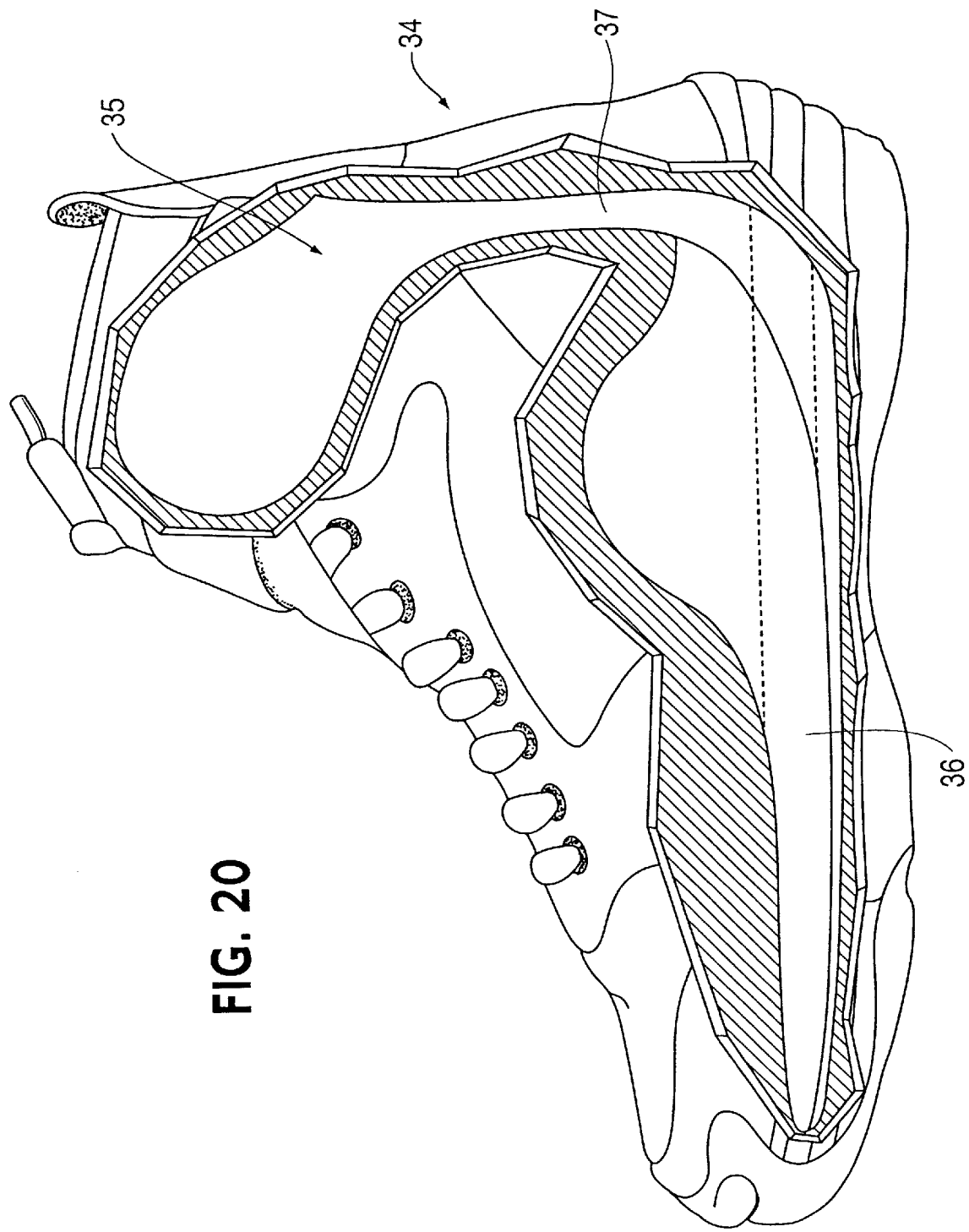

FIG. 20 is a lateral side view, partially cutaway, of a shoe according to a further embodiment of the invention wherein the heel-sole counter is formed of a plurality of segments within the shoe.

Figure 21:
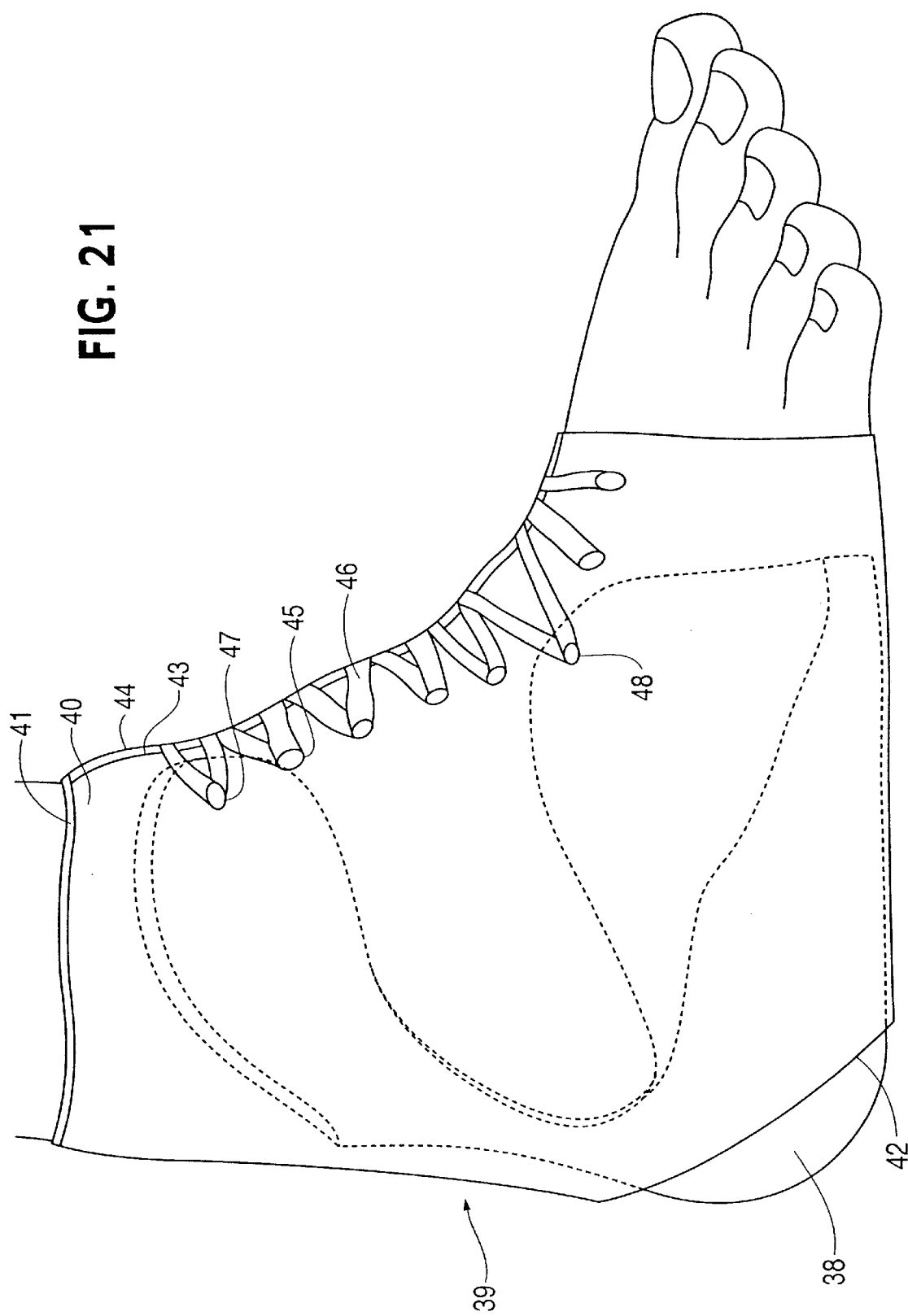

FIG. 21 is a lateral side view, partially cutaway, of an orthosis comprising a heel-sole counter of the present invention provided between and connected to two layers of material laced upon the foot.

DETAILED DESCRIPTION OF DISCLOSED EMBODIMENTS

Referring now to the drawings, anatomical considerations and biomechanical principles are briefly discussed in connection with FIGS. 1–6F of the drawings to aid in understanding the improved shoe, orthosis and method for protecting the ankle of the present invention as disclosed herein. The bony configuration of the ankle joint provides inherent stability. Essentially it is a hinge joint capable of movement in the sagittal plane, e.g. permitting plantarflexion and dorsiflexion of the foot with slight transverse plane motion occurring as well. The mortise of the joint comprises on one side the distal end of the tibia 55, the internal (medial) malleolus 53, and on the other side the distal end of the fibula 56, the external (lateral) malleolus 54. The moving component projecting into the mortis is the talus 57, which fits very tightly.

The malleoli, which hug the sides of the talus, are of unequal length and shape. The medial malleolus 53 is a short, stubby pyramidal structure whose tip extends only half way down on the body of the talus 57. The lateral malleolus 54 is rectangular and extends almost to the level of the talo calcaneal joint.

The body of the talus is not symmetrical. Its anterior portion is much wider than its posterior, so that when the foot is dorsiflexed the anterior portion abuts firmly against the two malleoli, creating a very stable situation. On the other hand, when the foot is plantarflexed the narrow posterior portion of the talus advances forward into the mortis and talar tilt occurs. This position produces lateral instability. When the foot is dorsiflexed the talus applies lateral stress to the lateral malleolus, forcing the fibula 56 outward. When the foot is both dorsiflexed and inverted, the side of the talus exerts even stronger pressure against the external malleolus.

Figure 1:
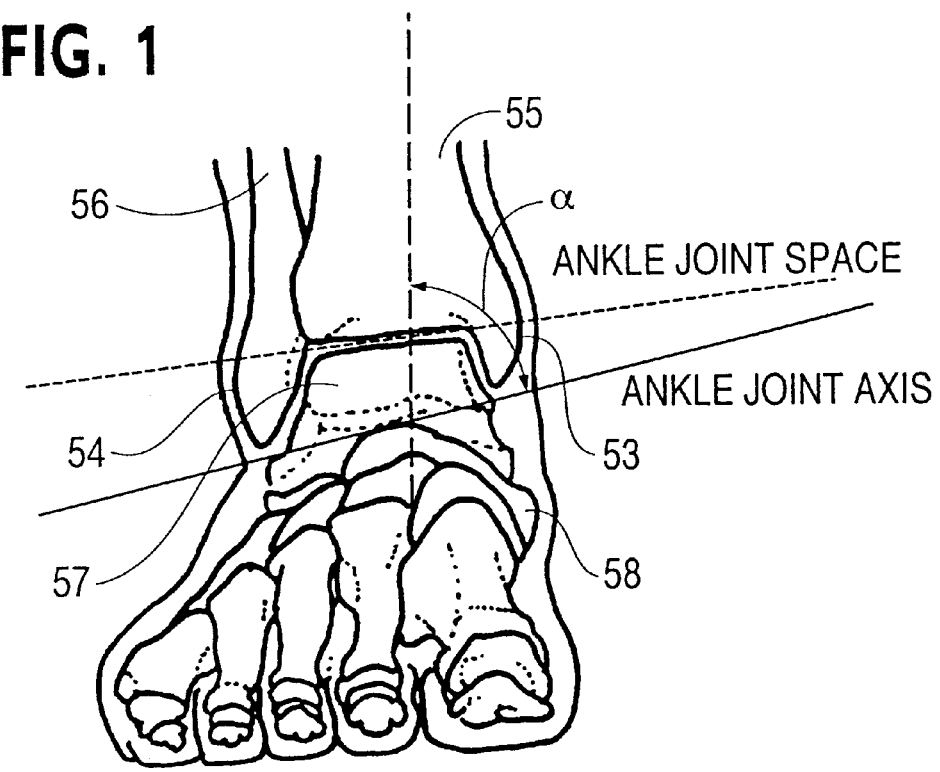
FIG. 1 is an anterior-posterior x-ray of the ankle joint complex.

The biomechanics of the ankle and foot are exceptionally important since these structures constitute the terminal portion of the limb. The ankle joint is the strategic location for the application of the muscle movements which initiate the forward swing of the limb and of those which cushion the application of the foot to the ground. Freedom of body movement requires an ankle joint which is flexible in more than one direction. For example, walking over irregular terrain would be almost impossible and probably disastrous if it were not for the ankle and foot being able to adapt themselves properly. The ankle talocrural joint is a synovial joint situated between the lower end of the tibia and the body of the talus (astragalus). The talus moves in the mortis formed by the internal malleolus of the tibia and the outer malleolus of the fibula as discussed above. The joint is considered by most anatomists to be a simple hinge which permits freedom of motion to occur primarily in the sagittal plane. This joint is capable of regulating the forward and backward fluctuations of the line of gravity so that it is kept within the limits of the supporting surface. Viewed from the front (frontal plane) the axis of this ankle joint on a normal subject is inclined downward from the medial to the lateral aspect as depicted in FIG. 1. It forms an acute angle $\alpha$, with the long axis of the tibia which has been found to vary from 68 to 88 degrees, with a mean of 80 degrees. The axis passes approximately three to five millimeters distal to the distal tips of both malleoli when extended laterally and medially. Because of the curvature of the trochlea (the articulating surface of the talus) there is no definite relationship between the axis of the ankle joint and the ankle joint space as seen in the anterior-posterior X-ray of FIG. 1.

This inclination $\alpha$ of the axis of the ankle joint results in the forepart of the foot being turned medially (adduction) on plantarflexion and laterally (abduction) on dorsiflexion. The amount of displacement depends on the inclination of the joint axis and the amount of plantarflexion or dorsiflexion attained. The amount of adduction during the period from heel strike to foot flat during walking is also dependent upon the inclination of the ankle joint axis. It has been shown that a person with flat feet and associated abduction may be helped by wearing higher heels. This is due to the higher heels inclining the ankle joint axis and elevating the hindfoot which causes greater plantarflexion in the ankle and therefore greater adduction.

Figure 2:
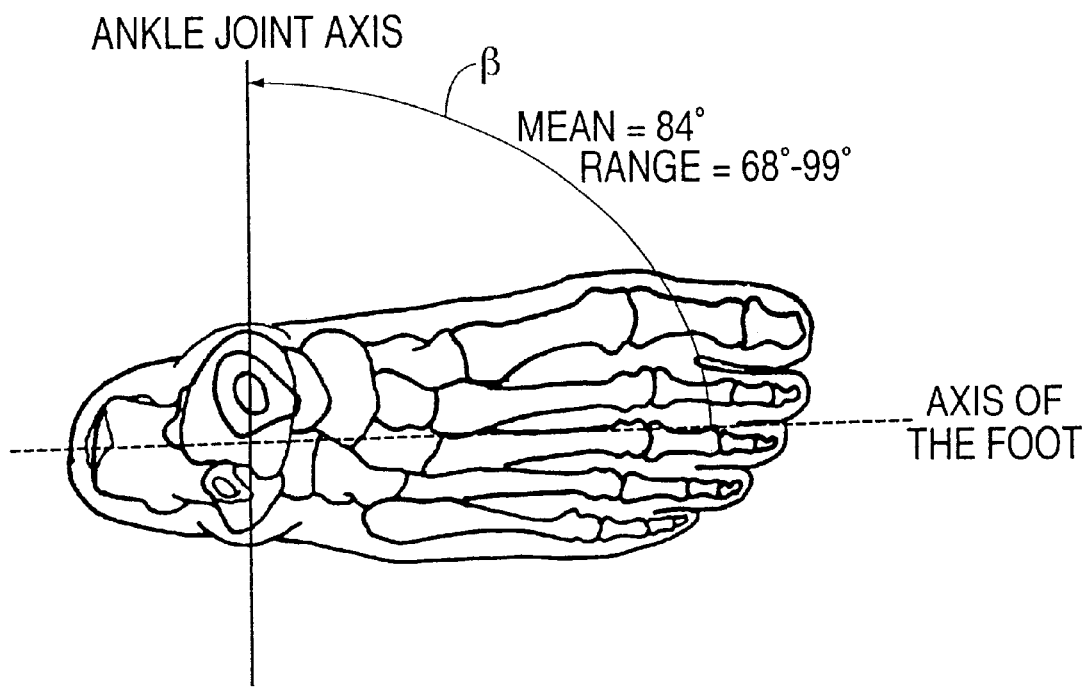
FIG. 2 is an x-ray from above of the ankle joint and foot for illustrating the angle between the axis of the ankle joint and the long axis of the foot, projected on a horizontal plane.

The angle $\beta$ in FIG. 2, between the axis of the ankle joint and the long axis of the foot as viewed from above (projected on a horizontal plane) also varies from person to person. This angle $\beta$ has been found to vary from 68 to 99 degrees with a mean of 84 degrees. The angle may be interpreted as indicating the amount of tibial torsion when the foot is fixed flat and the leg vertical under static conditions or it may affect the degree of adduction and abduction that the foot will adopt when the tibia and fibula are fixed in a standard position.

Open kinetic chain motions of the ankle joint are: plantarflexion with adduction and dorsiflexion with abduction. As reported in the Justin Wernick and Russell G. Volpe in *Lower Extremity Function and Normal Mechanics,* Chapter 1 of the textbook *Clinical Biomechanics of the Lower Extremities* by Ronald J. Valmassy, Mosby-Year Book, Inc., St. Louis, Mo. 1996, motions occurring in the closed kinetic chain require that movements be described as occurring only in those structures whose motion is not restricted by the presence of the ground. A motion described in the open kinetic chain at a given joint produces an equal and opposite motion proximal to the joint in question in the closed kinetic chain. This concept is essential to describing and understanding normal function of the foot and leg in gait. As most motions of the foot in gait occur with the foot on the ground, the classically described open chain motions of a given joint in the closed chain model with the distal segment bearing weight are observed as the proximal segment moving relative to it.

The subtalar (talocalcaneal) joint is located between the talus 57 and calcaneus 61 and permits motion of the foot in the frontal plane. Therefore, it is in position to regulate the side-swaying of the line of gravity. In particular, this joint allows inversion and eversion of the heel of the foot. The subtalar joint has been described as being composed of three facets on the inferior surface of the talus articulating with three facets on the superior surface of the calcaneous. The axis of the joint runs from posterior, plantar, and lateral, to anterior, dorsal and medial. The extent of motion occurring at the subtalar joint may equal that of the ankle joint. It is designed for activity such as walking on inclined surfaces or irregular ground. Such activities as getting into a car or turning the body while standing may require the full range of motion.

Figure 3A:
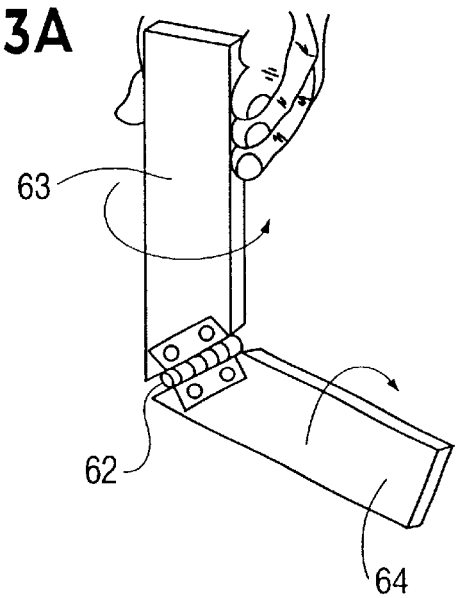
FIGS. 3A and 3B depict respective movements of segments connected by a mitered hinge for illustrating the function of the subtalar (talocalcaneal) joint.
Figure 3B:
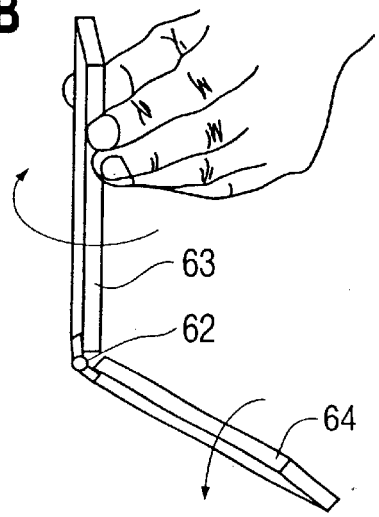

The subtalar joint functions essentially as a single-axis joint, and its angle (viewed from the side, projected on the sagittal plane) is such that it acts like an oblique, mitered hinge 62, see FIGS. 3A and 3B. Axial rotations of the leg 63 are directly transmitted to the foot 64 and vice versa. Internal rotation of the leg causes pronation (lowering the arch) of the foot and external rotation causes supination (raising the arch).

Figure 4:
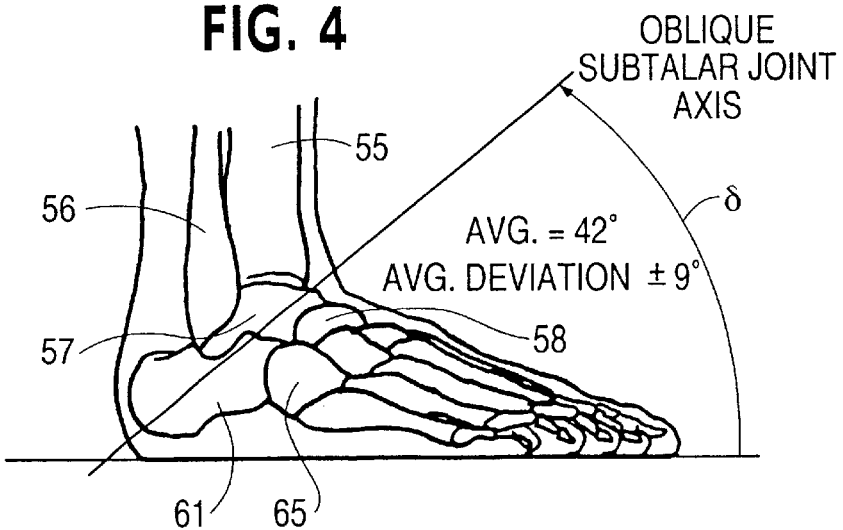
FIG. 4 is an x-ray of the foot and lower leg from the lateral side of the foot for illustrating the angle between the axis of the subtalar joint, as projected on the sagittal plane, and the horizontal.

When the angle, $\delta$ in FIG. 4, between the axis of the subtalar joint as projected on the sagittal plane and the horizontal is 45 degrees with the foot flat and the leg vertical, the coupled axial rotations of the leg and foot are equal in magnitude although they are acting in planes at right angles to each other. However, the inclination of the axis of the subtalar joint with the horizontal shows individual variations. The average angle $\delta$ has been reported as 42° with an average deviation of ±9° as shown in FIG. 4.

The effect of these variations in the angle $\delta$ of the subtalar joint axis to the horizontal is to alter the relation between the amount of pronation and supination of the foot and the amount of rotation of the leg about its longitudinal axis. The less the angle of inclination (when the axis is closer to the horizontal) the greater the pronation and supination imposed upon the foot by a given amount of axial rotation of the leg in respective directions. Where the axis of the subtalar joint is closer to the vertical, such as in the case of a person with a cavis foot, a specified amount of rotation of the leg about its long axis results in less pronation and supination of the foot.

The axis of rotation of the subtalar joint as projected on a transverse plane (viewed from above), referred to herein as the longitudinal axis of the subtalar joint in a top plan view thereof, also shows individual variations in the angle $\theta$ it forms with the long axis of the foot, see FIG. 5. The average angle for $\theta$ found by Inman was 23 degrees ±11°. Manter reported the average medial deviation in a transverse projection from the sagittal plane, the angle $\theta$, was 16°, with a range of 8°–24°. All the functional implications of the variations in this plane are not completely understood. It does appear clear that the greater the angle $\theta$ between the longitudinal axis of the subtalar joint (viewed from above) and the long axis of the foot, the greater will be the elevation (with adduction), and depression (with abduction), of the lateral side of the foot.

During normal locomotion, the segments of the thigh and shank undergo a series of rotations about their long axes. During stance phase, the rotations are only possible because of the action of the subtalar joint. The linkage provided by this joint requires that pronation or supination of the foot accompany the transverse rotations of the leg. Whereas motion at the ankle joint is readily perceived, the simultaneous motion of the subtalar joint is more difficult to see but it is of equal importance in normal walking.

Wernick and Volpe report in their *Lower Extremity Function and Normal Mechanics* that the three to one ratio of deviations of the subtalar joint axis on the frontal and transverse planes to deviation of the axis on the sagittal plane provides an easy formula for understanding the available motions in each body plane that may be expected in a normal subtalar joint. This ratio of deviations indicates that for every degree of sagittal plane motion there will be 30 of transverse and frontal plane motion. Thus, transverse and frontal plane motions predominate at the subtalar joint. This, taken with the sagittal plane motion available at the ankle joint, creates a rear foot complex of two major joints in close proximity which, together, have significant amounts of motion available in all three body planes to allow for smooth translation of the leg over the foot during gait.

It is further reported in *Lower Extremity Function and Normal Mechanics* that the motion available at the subtalar joint is triplanar, as the axis is deviated between all three body planes. The triplanar motions are known as pronation and supination. In open kinetic chain, with the foot free at the end of the leg, the components of supination are plantarflexion, adduction, and inversion.

Closed kinetic chain motion occurs at the subtalar joint throughout much of the stance phase of gait. This joint accommodates most of the rotation of the lower leg in closed kinetic chain where the foot is planted on the ground. Closed kinetic chain motion at the subtalar joint remains inversion with supination and eversion with pronation in the frontal plane. Wernick and Volpe report in their *Lower Extremity Function and Normal Mechanics* that no limitations on frontal plane motion of the subtalar joint are placed on the foot with weight bearing. That is, the subtalar joint and foot can easily invert and evert with the foot on the ground. However, the friction from the ground in closed kinetic chain prevents the foot from plantarflexing and abducting.

Figure 5A:
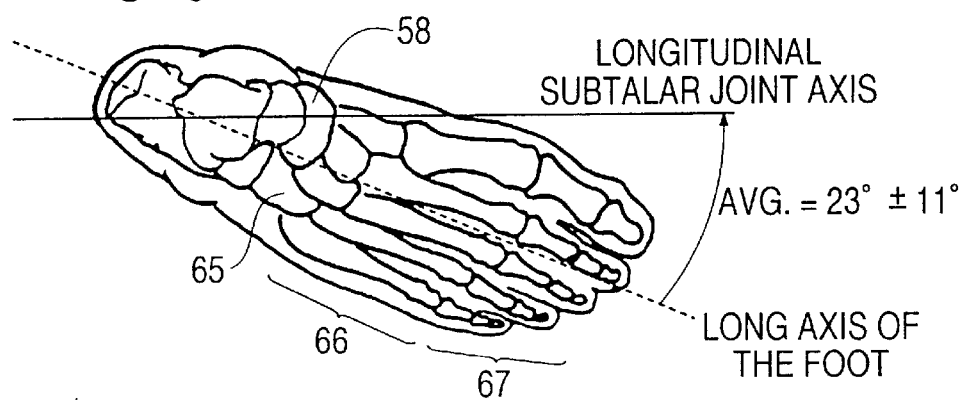
FIG. 5A is an x-ray from above the foot and ankle showing the angle between the longitudinal axis of the subtalar joint and the long axis of the foot, e.g. the subtalar joint axis as projected on the transverse plane, i.e. the longitudinal axis of the subtalar joint as seen in a top plan view thereof.
Figure 5B:
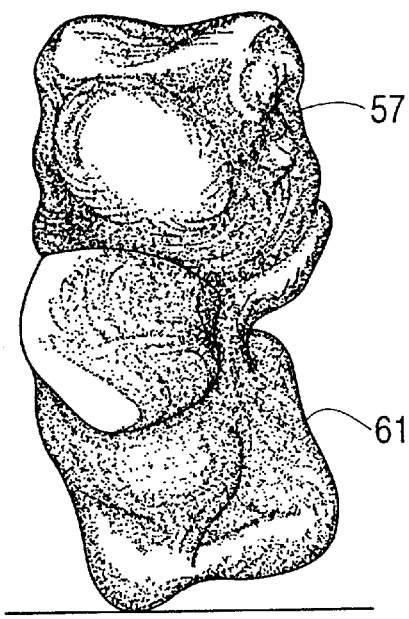
FIG. 5B is a frontal plane view of the rearfoot showing calcaneal inversion with talar abduction and dorsiflexion in closed chain supination of the subtalar joint and FIG. 5C is a frontal plane view of the rearfoot showing calcaneal eversion with talar adduction and plantarflexion in closed chain pronation of the subtalar joint (From Root M., Weed J., Orton W.; *Clinical Biomechanics Vol. II Normal and abnormal biomechanics of the foot,* Los Angeles, 1997, Clinical Biomechanics Corp.)
Figure 5C:
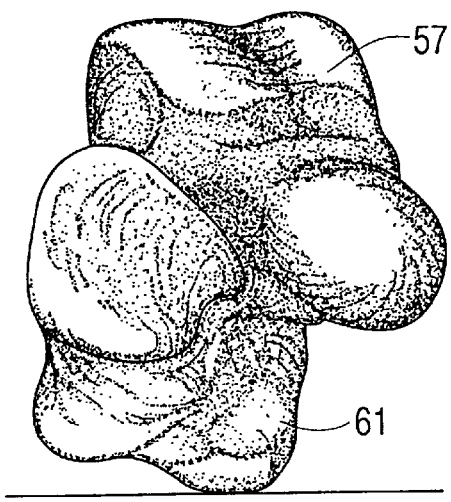

The transverse and sagittal plane motions which would occur in open kinetic chain are manifest in closed kinetic chain, with equal and opposite motions occurring proximal to the subtalar joint as noted above. Closed kinetic chain supination is therefore manifested as dorsiflexion and abduction of the talus which is just proximal to the subtalar joint, see FIG. 5B. Closed chain pronation of the subtalar joint is manifest with plantarflexion and adduction of the talus just proximal to the subtalar joint and eversion of the calcaneus as shown in FIG. 5C. The neutral position of the subtalar joint is described as that position of the joint in which the foot is neither pronated or supinated. From the neutral position, full supination of the normal subtalar joint inverts the calcaneus twice as many degrees as full pronation everts. It is stated in *Lower Extremity and Normal Mechanics* that the average subtalar joint neutral position is 0 to 3° inverted attitude of the calcaneus as measured relative to the lower ⅓ of the leg.

The average range of subtalar motion has been reported to be 30° with two-thirds (20°) in the direction of inversion and one third (10°) in the direction of eversion. It has been reported that throughout stance phase of gait, the average excursion of the subtalar joint is only 6°. This "functional range" of motion required for normal locomotion is considerably less that the aforementioned average range of motion available in the subtalar joint.

Figure 5D:
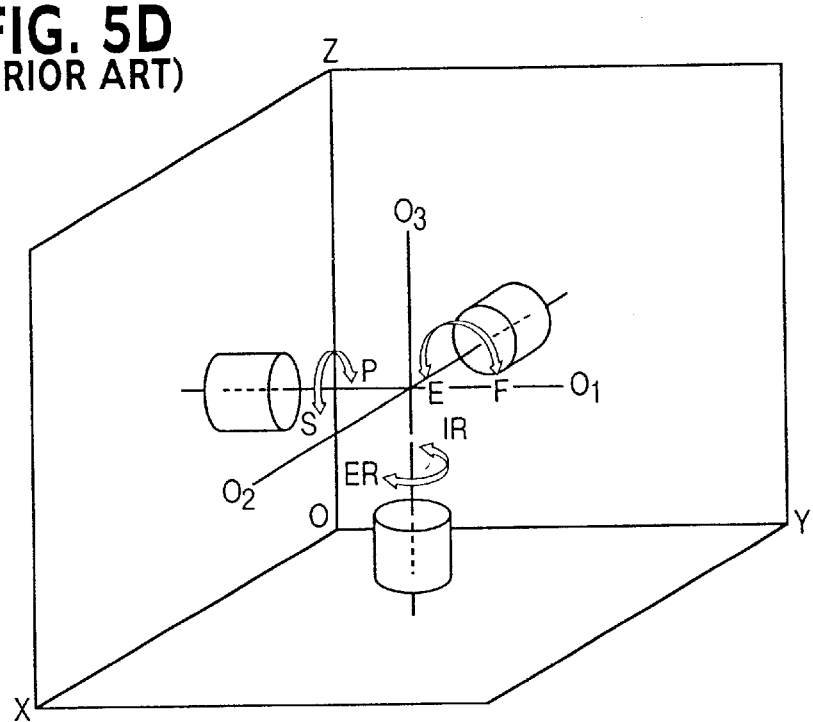
FIG. 5D is a schematic illustration of vectorial components of the subtalar joint axis of motion: Axis $0_1$, oriented longitudinally and generating the motion of supination-pronation; Axis $0_2$, oriented transversely and generating the motions of flexion-extension; Axis $0_3$, oriented vertically and generating the motions of internal rotation (adduction), external rotation (abduction). (From *Biomechanics of the Subtalar Joint Complex,* No. 290, May, 1993.)

FIG. 5D is an illustration from *Biomechanics of the Subtalar Joint Complex*, No. 290, May, 1993, depicting the vectorial components of the subtalar joint axis of motion. Axis $0_1$, oriented longitudinally is described as generating the motion of supination-pronation. Axis $0_2$, oriented transversely, generates the motions of flexion-extension. Axis $0_3$, oriented vertically generates the motions of internal rotation (adduction), and external rotation (abduction). The orientation of the subtalar joint axis of motion thus determines a triplanar motion of combined pronation-abduction-extension or supination-adduction-flexion, in the open kinetic chain as discussed above. During the stance phase of gait on even ground, the heel strikes with minimal inversion at the subtalar joint followed by eversion ranging from 5 to 10° at 10% of the walking cycle. From there, inversion occurs at the subtalar joint reaching a maximum of 5° at 62% of the walking cycle.

The transverse tarsal (midtarsal) joint of the foot should be looked on as an integral part of the subtalar joint because for normal motions to occur in the transverse tarsal and subtalar joints all three joints must be functioning in an normal manner. The midtarsal joint consists of the combined articulations of the talonavicular (57, 58) and calcaneocuboid (61, 65) joints. It represents the function articulation between the hindfoot (talus and calcaneus) and midfoot (navicular and cuboid). These articulations have been described anatomically as "plane" or "gliding" joints. Although the midtarsal joint is actually composed of two separate anatomic articulations, the transverse tarsal region is described as a single functional unit whose movement has been described as a segment rotating about two distinct axes of the midtarsal joint: the longitudinal and the oblique. Medial and inferior movements of the navicular and cuboid, on the talus and the calcaneus, respectively, are described with supination. In pronation, lateral and superior movements of the navicular and cuboid, on the talus and calcaneus, respectively, may be expected.

Figure 5E:
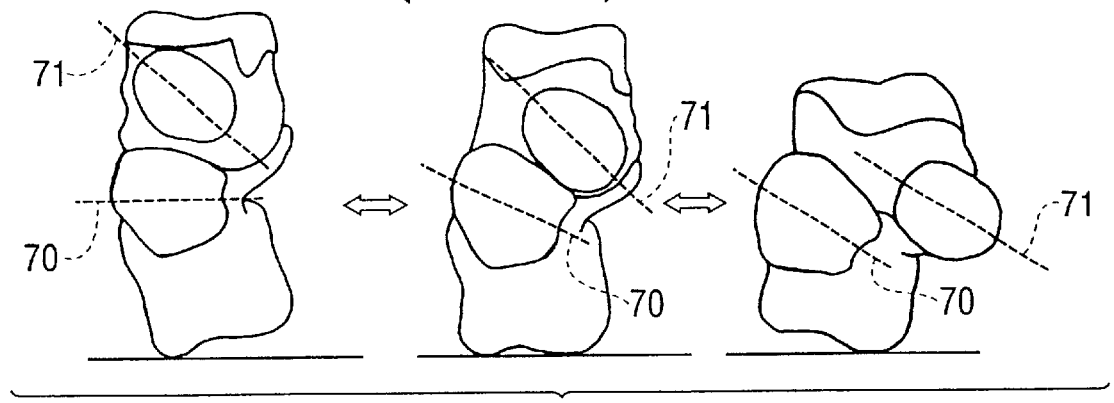
FIG. 5E illustrates that when the subtalar joint (STJ) is in its maximally pronated position (for right), the longitudinal axes of the articular facets of the midtarsal joint are lined up approximately parallel with one another. In the STJ neutral position, the angulation between the longitudinal axes has increased. Further divergence of the axes is noted on the far left with the STJ in its maximally supinated position. (From Seibel M: *Foot function, a programmed text,* Baltimore, 1988, Williams & Wilkins.)
Figure 5F:
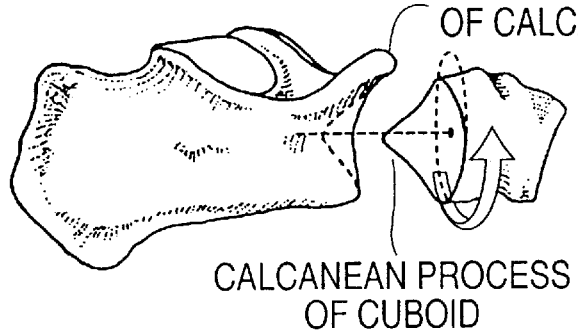
FIG. 5F schematically depicts the pronating cuboid pivoting about the calcaneal process until its dorsal border contacts the overhanging calcaneus. (From *Lower Extremity Function and Normal Mechanics* by Justin Wernick and Russel G. Volpe, adapted from Bojsen-Moller P; J. Anat 129; 165–176, 1979.)
Figure 5G:
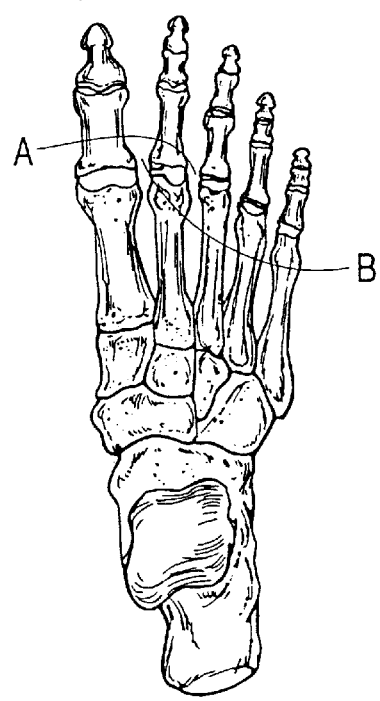
FIG. 5G depicts two different axes which exist in the metatarsophalangeal joint, a transverse axis (A), which corresponds to the high-gear axis, and an oblique axis (B), which corresponds to the low-gear axis. (From *Lower Extremity Function and Normal Mechanics* by Justin Wernich and Russel G. Volpe, redrawn from Bojsen-Moller, *Clin Orthop* 14:11, 1978.)

It has been further reported in *Lower Extremity Function and Normal Mechanics* that there is an interdependence of the subtalar and midtarsal joints. More particularly, the midtarsal joint range of motion is under the control of the position of the subtalar joint. This is apparent from FIG. 5E of the drawings which illustrates the relationship between the major axis 70 of the calcaneocuboid joint to the major axis 71 of the talonavicular joint in response to subtalar joint position. The left figure in FIG. 5E is similar to FIG. 5B and depicts the subtalar joint in a supinated position. The central figure of FIG. 5E shows the subtalar joint in a neutral position. The right drawing of FIG. 5E depicts the subtalar joint in pronation. As seen in FIG. 5E, in a significantly pronated subtalar joint, these axes 70 and 71 of the midtarsal joint take a more parallel orientation to each other facilitating increased range of motion of the fore foot on the rear foot. In a supinated subtalar joint, this parallel relationship is lost, and movements of the midtarsal joint about both axes are decreased.

The calcaneocuboid joint has been described as a concave-convex joint in the shape of half an hour glass. This structure facilitates rotation of the cuboid on the calcaneus with the calcaneal process serving as a pivot. Osseous locking occurs at the midtarsal joint when the pronating cuboid pivots about the calcaneal process until its dorsal border contacts the overhanging calcaneus as shown schematically in FIG. 5F. The ligaments of the midtarsal joint, which tighten in this pronated position, prevent further pronation beyond the osseous locking point. The location of the maximum lock position of the midtarsal joint as well as the range of motion of the midtarsal joint are affected by the subtalar joint position. As the subtalar joint becomes progressively more supinated, the maximal pronated position of the midtarsal joint moves in the direction of supination. As this more supinated position for end range of pronation is achieved, the midtarsal joint progressively locks, becoming more stable.

The metatarsal phalangeal joint is between the metatarsal heads 66 and the basal phalanges 67 of the toes. The joint, like the midtarsal joint, has freedom in three planes of motion. The motion in only one of these planes, flexion and extension in the sagittal plane, is under active voluntary control. It serves the finer adjustments between the toes and the metatarsals when the weight is thrown forward over the ball of the foot during push off. In the active propulsion stage of gait the metatarsal phalangeal joint becomes the active center of rotation for the foot.

A high-gear and low-gear mechanism have been described by which the heel-lift period of gait creates efficient propulsion for the foot. Two axes, a transverse axis A in FIG. 5G, composed of the first and second metatarsals, and an oblique axis B in FIG. 5G, composed of the second to fifth metatarsals, are described in this regard. Reportedly, the high gear is consistent with the transverse axis and the low gear is consistent with the oblique axis. The distance from the ankle joint to the oblique axis is shorter such that this axis is used first on heel-lift before the shift to the high-gear position. [*Lower Extremity Function and Normal Mechanics*, pages 5–48].

The diagrams of FIGS. 6A–6F show some of the forces and displacements that are associated with function of the subtalar and ankle joints during walking. Vertical force referred to in FIG. 6D is the force exerted in the vertical direction, i.e. directly downward. Fore and aft shear plotted in FIG. 6E are those forces which push forward (fore) and backward (aft) against the floor. Lateral shear denoted in FIG. 6F is that force which pushes medially or laterally against the floor. Torque is the twisting force due to the resistance of the rotation between the floor and the foot, see the directional arrows in FIG. 6C in this regard.

The stance phase of walking occupies the first 60% of the walking cycle as seen from FIG. 6A. It is suggested in the literature that during this phase the tibia, as it moves forward over the foot, remains in a parasagittal plane, not deviating medially or laterally. However, based on a thorough biomechanical analysis of this phase of gait, the present inventors believe that the lower leg deviates from mid-line laterally in this phase of the walking cycle. This is thought to be evidenced through the following mechanisms. The hip abductor muscles are going through an eccentric contraction thus acting as a guide wire which effectively pulls the knee laterally. This is directly associated with the fact that the medial femoral and tibial condyles are loaded more heavily than those of the lateral side. This is anatomically proven by the broadened articulating surfaces of these medial structures. It is also evident from the fact that the subtalar joint is supinating and or the talus moving into abduction which allows the calcaneus to invert thereby shifting the weight line more medial.

From 0 to 15% of the cycle, the foot plantar flexes on the leg and is placed flat on the ground; the tibia rotates internally; and weight is gradually applied to the foot until by the end of this period the foot is supporting 120% of the body's weight (due to forward momentum of the body), see FIGS. 6B and 6D. In this stage of gait the lower extremity is in it's maximum shock absorbing mode. The subtalar joint is pronating and the knee is flexing to absorb impact. At such time, the heel-sole counter mid portion torsion bar of the present invention as discussed hereinafter, acts as a shock absorber by allowing controlled or resisted subtalar joint pronation. This shock absorption mechanism advantageously decreases the traumatic forces at the knee and foot complex.

At the instant of heel strike, the foot is actually pushing backward (pulling) and medial to the floor. Both of these conditions change shortly however, to forward pushing (at 2% of cycle) and at 15% of the cycle lateral pushing due to a combination of external rotation of the tibia and the hip abductor mechanism previously mentioned. From 15% to 50% of the cycle, the foot dorsiflexes on the leg; the tibia is still externally rotating and torque is developed between the foot and the floor, see FIG. 6C. At the foot flat phase of the cycle (20%), vertical force begins decreasing until it reaches 80% of the body weight at midstance phase (35% of the cycle). Vertical force then begins to rise again until it reaches a maximum of over 120% at heel rise (50% of cycle). During this same period the foot is still pushing forward and laterally against the floor. This changes, however, at midstance when the forward pushing changes to backward pushing due to the body's center of gravity passing forward of the stance leg. This backward pushing reaches its maximum force at heel rise. During the end of the stance phase, when the foot is plantar-flexing sharply, the vertical force and muscle activity fall off markedly.

The ankle joint and subtalar joint work together in gait. As noted above, the ankle combines dorsiflexion with abduction and plantarflexion with adduction. The subtalar joint combines dorsiflexion, abduction, and eversion in one direction and plantar flexion, adduction, and inversion in the other direction. These combined subtalar joint motions are referred to as pronation and supination. The method of the present invention protects a person's ankle by limiting subtalar joint motion of the ankle. This is achieved by controlling the motions of segments of the subtalar joint fore and aft of the subtalar joint while permitting motion of the foot about the ankle joint. Inversion and/or eversion ankle injuries can thereby be prevented from occurring or recurring while not impeding normal ranges of motion in the ankle and subtalar joints which are necessary to walk, run or jump. This control is enhanced by also limiting the motion of the midfoot as discussed hereinafter.

A high-top tennis shoe 1 according to a preferred embodiment of the invention is depicted in FIGS. 7–13H. The shoe 1 protects a person's ankle while not impeding normal ranges of motion in the ankle and subtalar joints which are necessary to walk, run or jump. The shoe 1 comprises a high-top upper 2 and a heel-sole 3. A means for securing the shoe on a person's foot includes external strap 4 which is non-stretchable in length. The two ends 5 and 6 of the strap 4 are connected to the shoe at points on or about the lateral heel-sole of the shoe fore and aft of the axis of the ankle joint as seen in a top plan view of the foot. An intermediate portion 7, see FIG. 9A, of the strap 4 is free floating and is secured by means of a free floating loop 8 on the strap. The loop 8 is secured over the medial anterior aspect of the ankle by a second strap 9 on the medial side of the shoe. The second strap 9 is secured to the shoe at one end, passes through the free floating loop 8 and is adjustably connected to adjust the tension in external strap 4 by means of a VELCRO closure 10 on the medial side of the shoe.

The location of the external strap 4 is selected such that its application of force to the foot is as close to perpendicular to the axis of the subtalar joint as shoe design and anatomy will allow. The external strap 4 is supported by the anatomy and the shoe 1. This moves the strap 4 further away from the subtalar joint axis of rotation and as a consequence a leverage produced by the tensioned strap is sufficient to control subtalar joint supination in combination with the supporting structure of the shoe. As stated above, in the disclosed embodiment the two distal origination points of the strap ends 5 and 6 are on either side of the axis of rotation of the ankle joint as viewed from above projected on a horizontal plane as shown in FIG. 2. In particular, their distal attachment points are located at the mid coronal plane of the calcaneus and at the base of the fifth metatarsal head. As a consequence, plantarflexion and dorsi-flexion of the ankle joint doesn't significantly alter the length requirements for the external strap 4. In dorsiflexion as the tibia and fibula move forward the posterior attachment point at end 6 on the lateral calcaneal buttress or wedge 29 moves downward keeping the tension on the strap 4. If the applied direction of force on the strap 4 is somewhere between its two distal and proximal attachment points, then its applied force is somewhat parallel to the axis of rotation of the ankle joint and as a consequence, its tension isn't greatly influenced by the aforementioned ankle joint motions. Further, the distal anterior attachment of forward end 5 of the external strap 4 at flared lateral buttress or wedge 30 is preferably further anterior of the ankle joint than the posterior attachment is posterior thereto. This permits the strap 4 to become less tensioned in dorsiflexion. As noted previously, dorsiflexion is a stable positioning reference to subtalar joint motions. With such an arrangement, the strap 4 becomes increasingly tensioned when the foot is plantarflexed which is when it is needed the most. The tensioned external strap 4, secured by second strap 9 and free floating loop 8 functions to prevent the lateral distal side of the shoe from moving distal or down in relation to the proximal medial aspect of the upper.

This strap arrangement is effective in doing this when the ankle joint is plantarflexed or dorsiflexed because its intermediate portion 7, FIG. 9A, is free floating and connected by free floating rectangular loop 8 which preferably has a roller pin 11, see FIG. 9B, or roller sleeve 12, see FIGS. 9C and 9D, contacting the intermediate portion 7 of the strap 4 to permit relative movement between the rectangular loop or cylinder device and the strap 4. Preferably, the non-stretchable strap 4 includes a change of material to TEFLON or some other low friction material in the intermediate portion 7 contacting the loop 8. Thus, the strap 4 is effective in performing the aforementioned function when the ankle joint is plantarflexed or dorsiflexed. The angle and direction of pull of the strap 4 prevents the lateral side of the shoe from moving distal in relation to the ankle. It is positioned on the outside of the shoe upper because this increases the distance from the axis of rotation of the subtalar joint, thus producing a better mechanical advantage.

Figure 12:
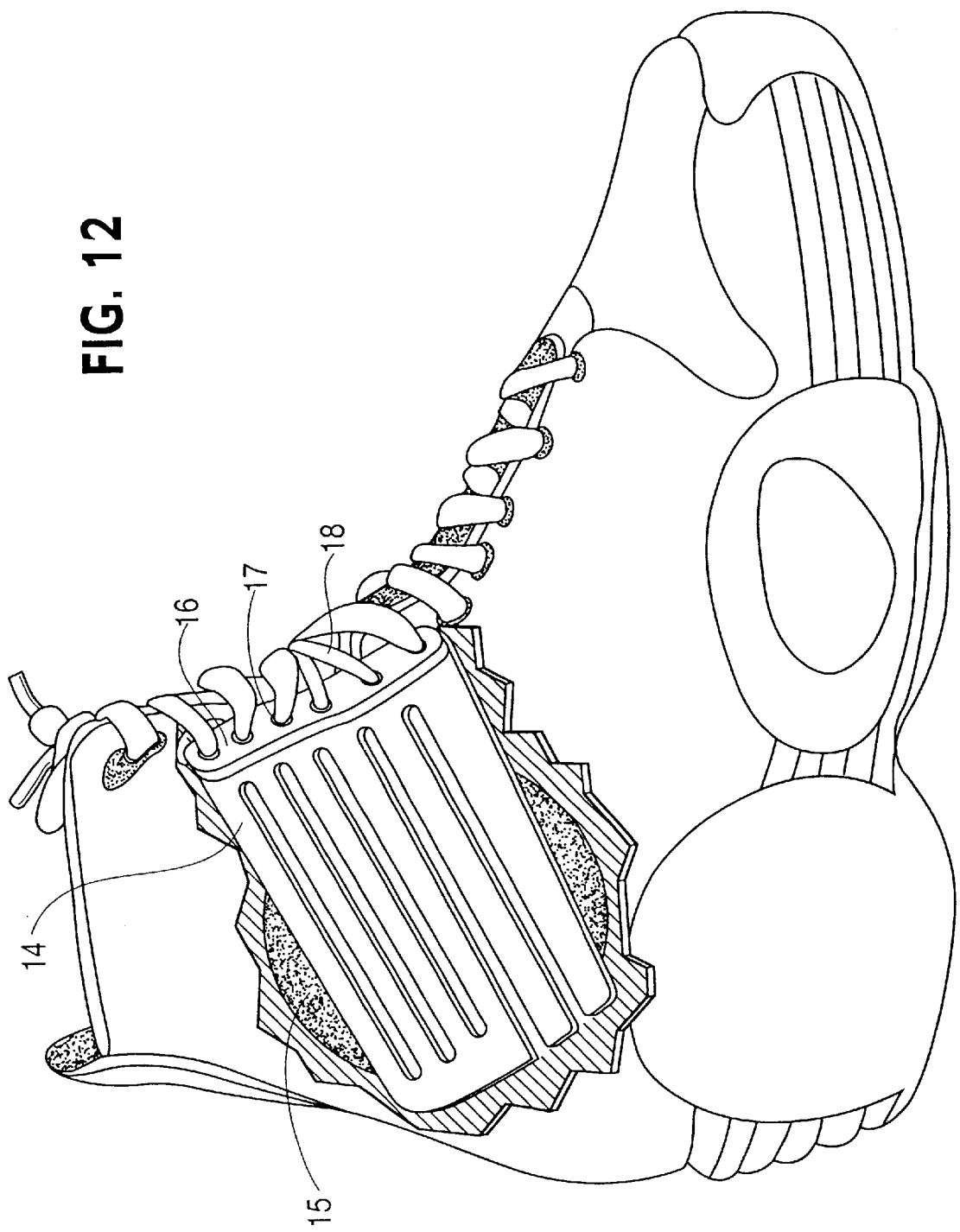
FIG. 12 is a lateral side view of the shoe like FIG. 11 but depicting an expansion joint sewn or otherwise formed in the sidewall of the upper and extending over the lateral malleolus pad or air bladder of FIG. 11 from one side thereof around the laces to the opposite side for bolstering the sidewall of the shoe, together with the heel-sole counter, against supination.

The strap 4 also produces a clockwise directed torque on the upper 2 and heel-sole counter 13, see FIGS. 13A–13H. This torque is neutralized by the use of an expansion joint 14 integrated in the side wall of the upper 2 as shown in FIG. 12 to act as a safety net to stop over supination in combination with the other features of the shoe as disclosed herein. The expansion joint 14 also acts as a bolster for an underlying lateral malleoli pad or air bladder 15 included in the side wall of the upper, see FIG. 11. At the lace end 16 of the expansion joint 14, the expansion joints are constructed as one continuous piece. The lace holes 17 therein are preferably raised in relation to the plane of the expansion joint and create a smooth transition for shoe laces 18 to make their transitions. The raised lace projections are interconnected to give the shoe a vertical support appearance in the disclosed embodiment. At the posterior end of the expansion joint 14, the expansion joints can be separate and/or continuous as shown in FIG. 12. This expansion joint 14 can be formed of a flexible strong fabric, vinyl, or plastic material.

As noted above, the strap 4 is free floating between its respective ends 5 and 6 so that it can articulate and move one strap in unison with the other when tensioned by means of closure 10, second strap 9, and free floating loop 8, even when the ankle joint is plantarflexed or dorsiflexed. The external strap 4 prevents shoe rollover by being non-stretchable in length and by having its origination points 5 and 6 on or about the heel-sole and its proximal termination point supported by a semi-rigid non-collapsible support structure as discussed hereinafter. The downwardly and medially directed force of the tensioned external strap 4 on the upper anterior portion of the ankle also aids in limiting dorsiflexion and abduction of the talus which occur in closed kinetic chain supination of the subtalar joint. This force also enhances the downward and rearward positioning of the foot with respect to the heel-sole counter 13 of the shoe in combination with the restraint provided by the conventional, tied shoe laces 18 of the shoe 1. Preferably, subtalar joint movements are stopped before the axis of their rotations is shifted beyond the normal range of motion of the joint as referred to above and to the side of the projected weight line of the shoe such that shoe rollover, which is the byproduct of subtalar joint movement, will not occur.

The heel-sole counter 13 in the embodiment of FIGS. 7–13H is fabricated from a plastic material and to produce its desired affect it is trimmed asymmetrically. For example, the heel-sole counter could be fabricated from 5/32 or 1/8 inch thick copolymer thermoformed plastic such as polypropylene, or it could be fabricated by injection molding a suitable plastic material. The design of the heel-sole counter 13 reflects specific trim lines which promote specific movements and restrict unwanted movements. The heel-sole counter could also be formed symmetrically, but with asymmetric physical properties, to form a heel-sole counter with semi-rigid, shape-retaining characteristics for achieving the functions described below.

Figure 13A:
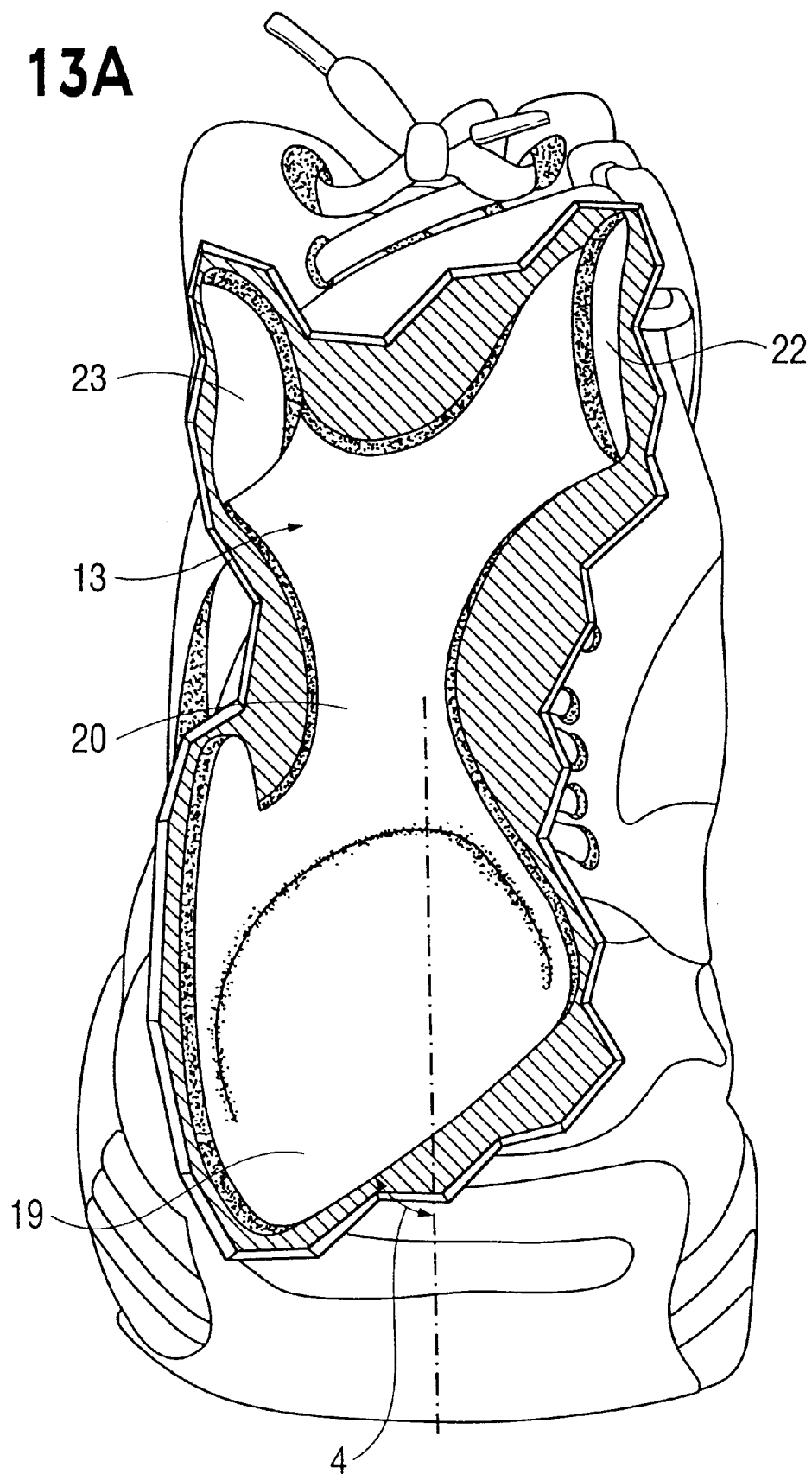
FIG. 13A is a front view of the shoe of FIG. 7 with a portion of the shoe cutaway to depict one form of a heel-sole counter of the invention, a short version, within the shoe.

The plantar surface 19 of the counter 13 is trimmed long on the lateral side and short on the medial side creating a leading edge which makes a 30–45° angle ψ, FIG. 13A, with a mid-sagittal plane of the foot. This angulated trim promotes eversion of the subtalar joint. The medial side of the counter about the heel is effective to limit inversion of the rear portion of the calcaneus in supination beyond the normal range. Likewise, the lateral side of the counter extends forward and upwardly to limit abduction of the forward, anterior portion of the calcaneus and the talus in supination beyond the normal range.

The posterior of the calcaneal and the achilles tendon trims (posterior strut 20) in the preferred embodiment are also asymmetrical. The medial trim of strut 20 is trimmed closer to the mid-sagittal line than the lateral trim. This asymmetrical trim of the posterior strut angulates the ankle joint into slight eversion when the foot is dorsiflexed. The posterior strut 20 is wider in the medial-lateral direction than it is thick in the anterior-posterior direction. As a consequence, it resists medial and lateral collapse. However, it moves relatively freely into dorsiflexion and with slight resistance into plantarflexion. The ankle joint axis of rotation is externally rotated to the line of progression of the foot as discussed previously and as illustrated in FIG. 2 of drawings. The asymmetrical trim lines of the heel-sole counter 13 reflect this and promote movement on this axis of rotation. This movement is adjustable by varying the width and thickness of the strut 20. The strut design resists vertical collapse and also resists internal and external rotation in the transverse plane of motion. More specifically, in the disclosed, preferred embodiment of the invention, the inclination of the subtalar joint axis with respect to the horizontal and also the inclination to the long axis of the foot as depicted in FIGS. 4 and 5 as well as its location, are taken into consideration to create a support structure for the foot which will prevent unwanted motions and encourage wanted motions.

Figure 13D:
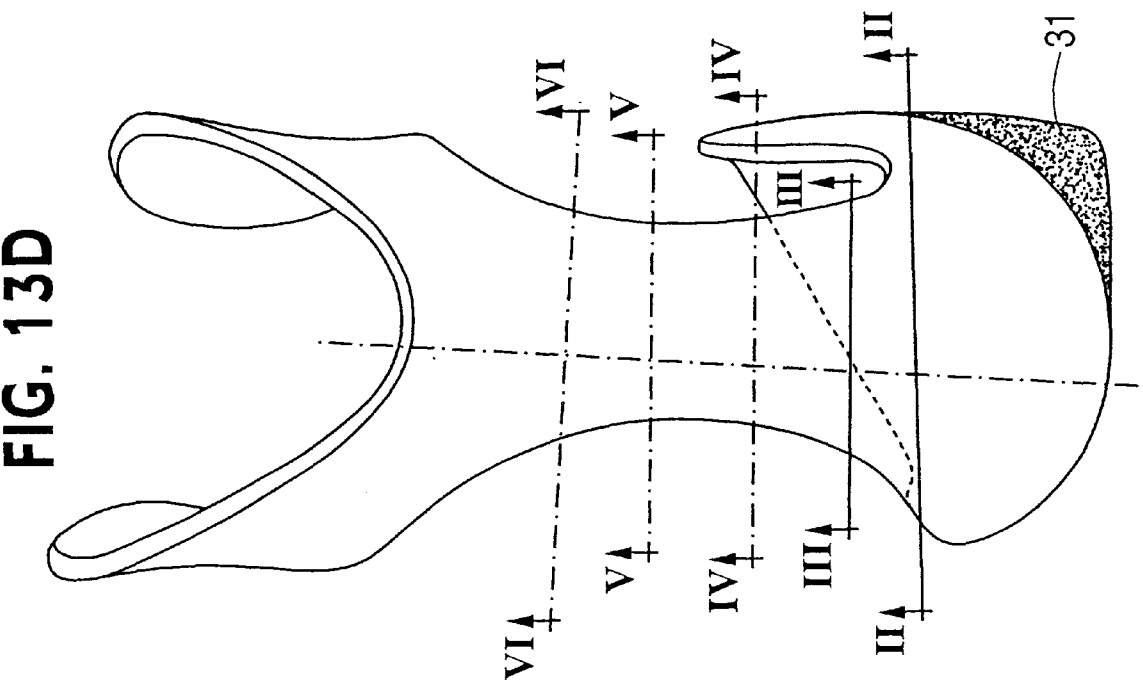
FIG. 13D is a posterior view of the heel-sole counter of FIG. 13C wherein a lateral heel wedge buttress has been added for additional stability.
Figure 13C:
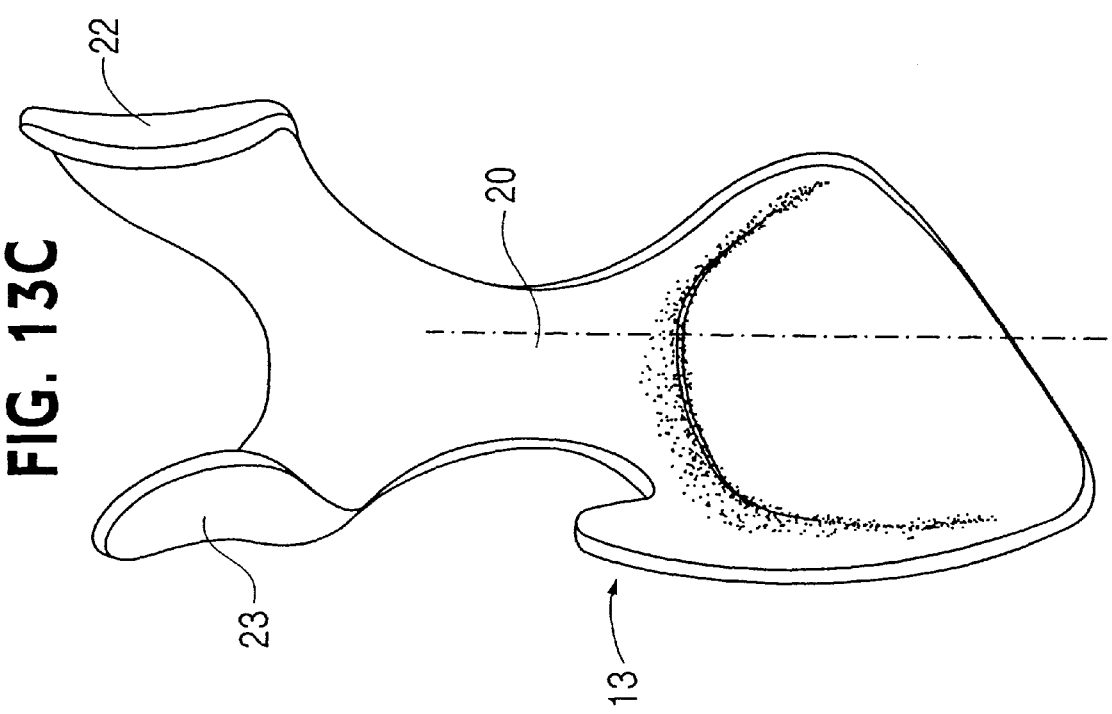
FIG. 13C is a front view of the heel-sole counter in the shoe of FIGS. 7, 9A, 13A and 13B, before the heel-sole counter is combined with the shoe.
Figure 13E:
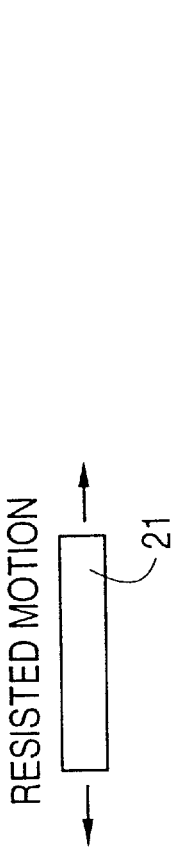
FIGS. 13E and 13F are schematic drawings of respective torsion bars, shown in transverse cross section, for describing the asymmetrical properties of a torsion bar employed in the heel-sole counter and shoe in limiting subtalar joint motion while permitting motion of the foot about the ankle joints.
Figure 13F:

The transverse plane views of a vertical beam 21 of FIGS. 13E and 13F depict how motions in the directions of the arrows are encouraged or resisted by a torsion beam which has an asymmetrical cross section, rectangular in the illustration example. Movement to be encouraged utilizes the narrow side of the rectangular structure as illustrated in FIG. 13E. The wide part of the beam resists motion, FIG. 13F. The inside of the posterior of the heel-sole counter 13 is provided with a posterior pad, not shown, calcaneal in shape on the inside for supporting the heel, the pad extending upwardly along the inside of strut 20 to the top of the posterior of the counter 13 for cushioning against the heel, achilles tendon and the posterior portion of the lower part of the leg.

Figure 13G:
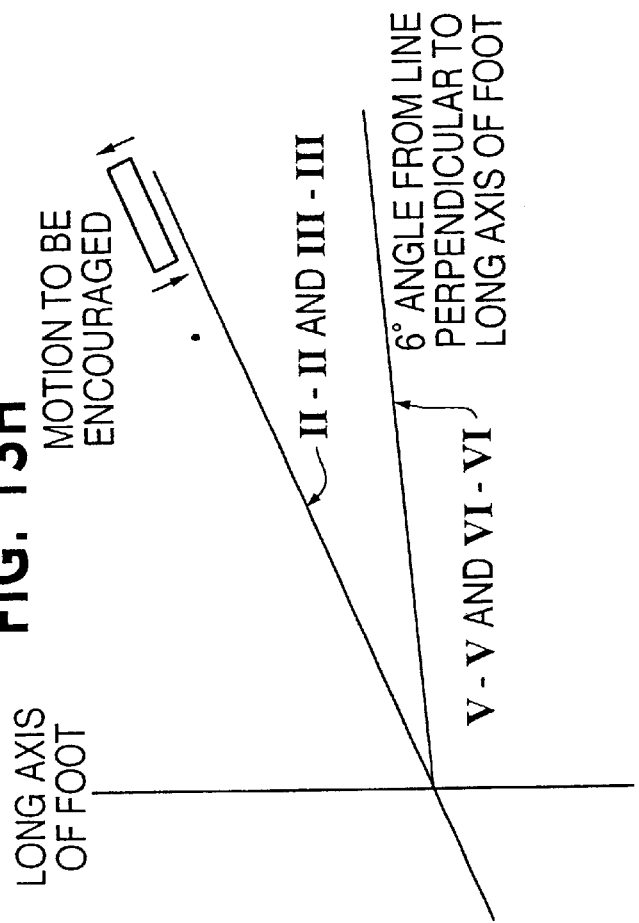
FIGS. 13G and 13H are schematic illustrations of a right foot transverse plane view with the long axis of the foot and the longitudinal axis of the subtalar joint, as seen in a top plan view thereof, shown in relation to each other and the preferred directional relationship of the torsion bar thereto in selected cross sections II—II through VI—VI of FIG. 13D.
Figure 13H:
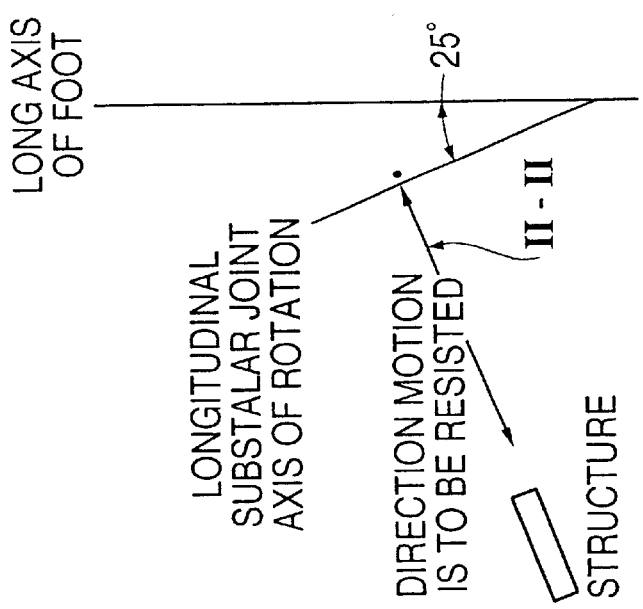
Figure 14A:
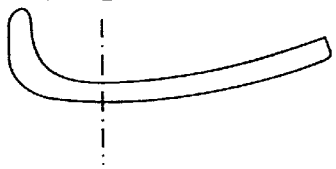
FIGS. 14A through 14E are respective cross sectional views through other torsion bars having different configurations which could be used as part of the heel-sole counter and shoe or orthosis of the present invention.
Figure 14B:
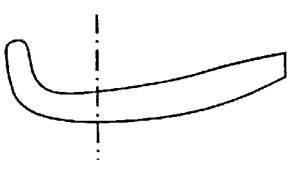
Figure 14C:
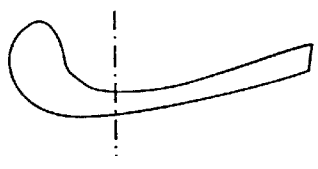
Figure 14D:
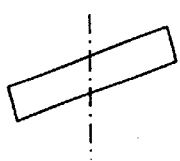
Figure 14E:
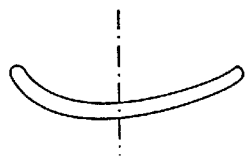

It is shown in cross sections II—II and III—III, see FIGS. 13D, 13G and 13H that the posterior of the counter 13 in the vicinity of the heel and the lower portion of strut 20 adjacent the heel, is preferably shaped to reflect an internal rotation angle with respect to the long axis of the foot i.e. rotated in the direction of the longitudinal axis of the subtalar joint as seen in a top plan view thereof. The angle of rotation is preferably at least several degrees to as much as 23° or more such that the direction of the torsion bar most resistant to bending motion is orthogonal or nearly orthogonal to the longitudinal axis of the subtalar joint as seen in a top plan view thereof. As a result, rotation of the lower portion of the counter 13 about the longitudinal axis of the subtalar joint can be effectively resisted or limited. The angle is 23° in the disclosed embodiment, which reflects the line drawn perpendicular to the average angle of the longitudinal axis of the subtalar joint to the long axis of the foot as seen in the top plan view of FIG. 5. This orientation provides maximum resistance to torsional motion of the lower portion of the counter 13 and the foot about the longitudinal axis of the subtalar joint to limit supination of the subtalar joint to an amount preferably less than or equal that allowed in a normal range of motion of the joint.

The strut 20 in the disclosed embodiments is progressively twisted in the frontal plane direction along its length from above the region of the heel to the upper end of the strut adjacent wings 22 and 23 to be secured about the lower leg. As seen in the cross sections V—V and VI—VI of FIGS. 13D and 13H, the strut 20 is progressively twisted in the direction of the frontal plane until its direction of the elongation has gone from 23° internally rotated to an angle of 6° externally rotated with respect to the long axis of the foot for encouraging motion of the foot about the ankle joint. See FIG. 2 wherein the mean angle of the ankle joint axis with respect to the axis of the foot is 84°. Thus, the narrow side of the rectangular beam as schematically illustrated in FIG. 13E is oriented for most effectively encouraging motion of the foot about the ankle joint axis.

In one construction of a heel-sole counter 13, a posterior strut or torsion bar 20 was made by holding its distal segment in a vice, the plastic was heated 1½ inches proximal to the vice, the plastic was then rotated in a counter clockwise direction 23° and then 1½ inches above this it was rotated clockwise 17°. The plastic was then cooled.

The proximal end of the counter 13 serves as anchor points or supports for the arrangement of straps 4 and 9 and the upper portion of the shoe attached thereto. The counter is designed to resist vertical buckling which is needed to keep the medial side of the upper of the shoe from collapsing in inversion or shoe rollover. It terminates proximally at a cosmetically acceptable and sufficient leverage producing height, preferably at least several millimeters above the medial and lateral malleoli, 53 and 54, respectively. The medial and lateral flanges 22 and 23 can terminate at the same or different heights. However, the lower aspects of these flanges are preferably trimmed asymmetrically to allow clearance for the medial and lateral malleoli which are asymmetrical in their anatomical positions.

The shape of the posterior strut 20 of the heel-sole counter 13 may be symmetrically or asymmetrically arranged with respect to the longitudinal axis of the foot posterior of the achilles tendon and can have a variety of asymmetric or symmetric configurations as seen in transverse plane view, see the examples of 14A–14E. However, preferably its directional properties in resisting and encouraging motion as generally discussed with reference FIGS. 13E and 13F are asymmetric with respect to the long axis of the foot for more effectively resisting torsional movement of the lower portion of the heel-sole counter about the longitudinal axis of the subtalar joint in supination to prevent roll over while permitting or encouraging motion of the counter and foot about the ankle joint.

The semi-rigid, heel-sole counter 13 promotes wanted motions and prevents or limits unwanted motions as discussed above. It has energy storing capability such that after flexing to allow wanted motions in response to an applied force, the semi-rigid counter exhibits a shape-retaining character and returns to its original configuration in the shoe upon release of the applied force. In the disclosed embodiment, the heel-sole counter is integrated into the shoe 1 as it is inserted between inner layer 24 and outer layer 25 of the upper 2 utilizing industry standard positioning and construction methods during manufacture of the shoe. The upper terminates at its proximal end at an anatomical, cosmetically acceptable height to provide good leverage. The layers 24 and 25 of the upper may be fabricated of leather, vinyl, soft open or closed cell foams and, in combination with the heel-sole counter 13 therein are constructed to achieve lateral ankle stability.

Figure 15A:
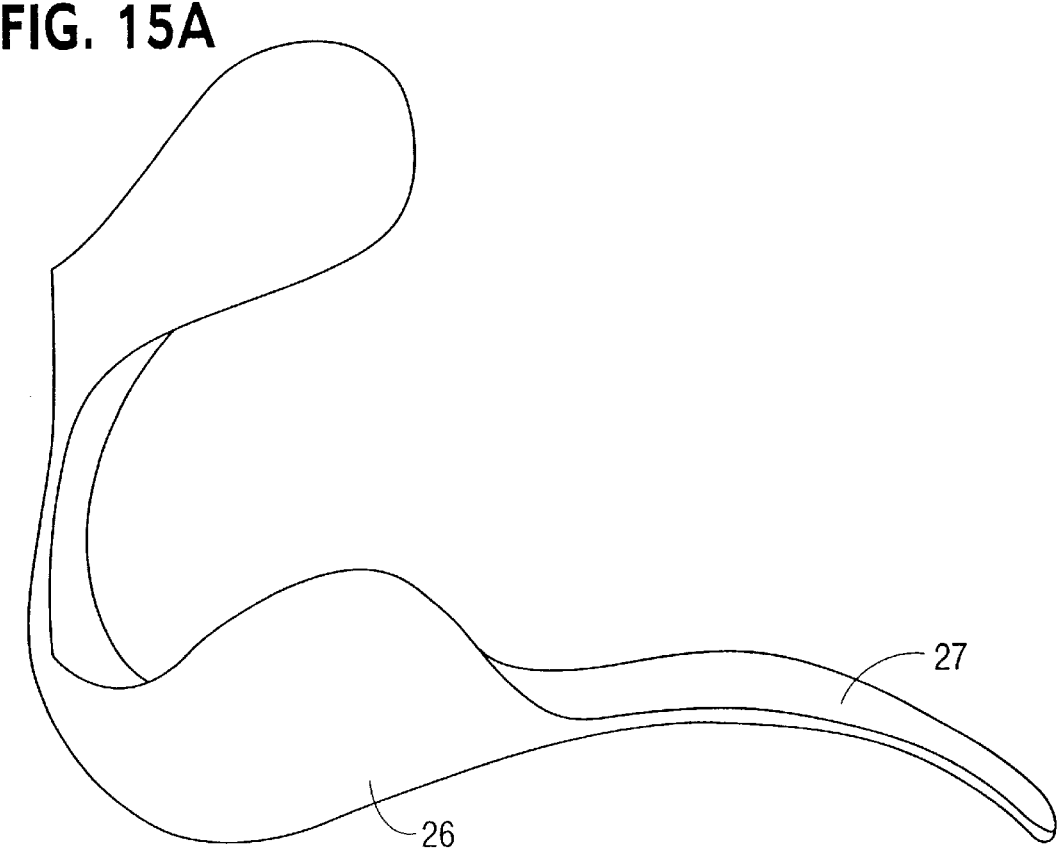
FIG. 15A is a lateral side view of another embodiment, a long version the heel-sole counter for use in the high-top tennis shoe of the invention of FIG. 7 in place of the short version of FIGS. 13A–13D, wherein the counter is extended forward in the shape of an upwardly arched, single leaf spring for supporting the foot within the shoe.

The heel-sole counter 26 shown in FIGS. 15A and 15B may be used in the shoe 1 of FIG. 7 in place of the heel-sole counter 13. This is shown in FIG. 16 where shoe 28 is like shoe 1, except for the use of the long version of the heel-sole counter of FIGS. 15A and 15B in place of the short version of FIGS. 13A–13D. The counter 26 is like counter 13 except that it has a long foot plate extension 27 which is molded into the shoe sole's construction. The long foot plate extension 27 is in the shape of a single-leaf, upwardly arched spring. At the distal aspect of the calcaneus it narrows in width and starts a proximal transgression peaking at the midfoot and then progressing on a downward trend making an arc with the apex of the arch located at the midfoot. In the fabrication of the shoe, this leaf spring of the extension 27 is flattened (pre-loaded) and the sole is attached for construction of the shoe 28 as depicted in FIG. 16. This pre-loading or storing of energy provides assistance during the stance phase heel off portion of gait, running or jumping activities. This potential stored energy can improve athletic performance. The distal end of the extension 27 is preferably trimmed as shown generally in FIG. 15B, in conformance with the locations and directions of the transverse and oblique axes of the joint between the forefoot and midfoot as discussed with reference to FIG. 5G, so as not to interfere with the flexibility of this joint, e.g., flexing and extending motions of the foot segments distal to the midtarsal joints.

The heel-soles 3 of the shoes 1 and 28 are preferably designed to have a heel height from 0–⅜ inch, heel height being the difference between the thickness of the sole and heel. The flared lateral non collapsible heel wedge or buttress 29 and the flared lateral non-collapsible sole wedge or buttress 30 located at the base of the fifth metatarsal head are formed as part of the heel-sole and sidewall of the upper of the shoe 2 as shown in FIGS. 9A, 10, 11 and 12, for example. The heel-sole counter 13 could also be formed with such a flared lateral non-collapsible wedge or buttress 31 as depicted in FIG. 13D, the wedge or buttress extending along the entire length of the lateral side of the counter at the heel-sole. These wedges or buttresses place the ankle joint in a stable position and shift the weight line laterally which prevents the heel-sole of the shoe from turning over and predisposing the subtalar joint to excessive harmful inversion. Thereby a mechanical function of these structures is to resist the clockwise directed torque of inversion (right foot as viewed from the posterior). It does this by shifting the weight line lateral of the axis of rotation of the subtalar joint. It also functions to keep the wearer's shoe more lateral by creating a laterally directed force on the shoe's heel-sole counter. The desired results have positive influences on inversion torque control. The wedge's distal segment which may be flat and parallel to the plantar surface of the foot, can be angled 1 to 5 degrees up on the lateral side as is the case with the wedge 29 in FIG. 10, for example. Such an angular cut keeps the wedge off the shoe's heel surface, which decreases the weight shift line principle, in normal activities. However, if the wearer's foot supinates, the wedge or wedges become an effective brake to slow this motion, i.e. become effective only when needed. As a consequence, the resulting force capabilities of the wedges are resistive and stoppage in nature. The heel wedge 29 located on the lateral aspect of the distal calcaneus also functions to keep the foot from sliding laterally off the foot bed of the shoe. This prevents the heel-sole 3 of the shoe from migrating medial in relation to the axis of rotation of the subtalar joint, which would cause inversion torque and in many instances uncontrollable torque which results in injury.

An insert 32 depicted in FIGS. 17–19 is also preferably provided inside the shoe. The insert is removable and has significant thickness in the heel and sole areas, ¼ inch–½ inch, and it is adjustable. It is preferably fabricated from a closed cell flexible foam material in a neutral anatomical position in relation to inversion and eversion. Its distal surface has identifiable markings represented by the dashed lines 33 in FIG. 17 which are also visible in FIGS. 18 and 19 as solid lines. These markings draw out a medial heel wedge $A_1$, medial heel and sole wedge $A_2$, lateral heel wedge $B_1$, and lateral heel and sole wedge $B_2$. The medial and lateral sides of the insert have corresponding lines to the previously mentioned wedges. Two sets of lines are utilized. The distal line reflects a ⅛ inch wedge cut and the more proximal line a ¼ inch wedge cut. These lines are utilized as guides so the trainer, user, orthotist, etc. can shape, grind or modify the insert to post the foot in inversion or eversion which positively influences subtalar joint torque.

The heel-sole counter 13 of the shoe 2 has a one-piece or integral construction. However, the heel-sole counter can be formed of a plurality of segments which are effectively supported in relation to each other by the remainder of the shoe or orthosis in which it is employed. Illustratively, the shoe 34 in FIG. 20 comprises a heel-sole counter 35 formed of a mid-sole segment 36 and an upper heel-sole segment 37 which are secured in relation to each other in the construction of the heel-sole and upper for effecting the desired control of subtalar joint motion as discussed with respect to the heel-sole counter 13 of shoe 2.

An orthosis 39 according to the invention is shown in FIG. 21 of the drawings. The orthosis comprises a heel-sole counter 38 similar to the heel-sole counter 13 employed in the shoe 2 as discussed above. The counter 38 is sandwiched between inner and outer layers 40 and 41 of the orthosis. The layers are preferably formed of a strong fabric, of a natural or synthetic material. The layers have an opening 42 for the heel portion of the counter 38 and opposed edges 43 and 44 over the anterior portion of the ankle. These edges include eyelets 45 for shoelaces 46 used to secure the orthosis about the ankle of the user. A hole 47 is provided in each of the upper flanges of the counter and a hole 48 is provided in the upper, lateral side of the lower portion of the counter. These holes cooperate with eyelets 45 to allow the lace 46 to extend therethrough for connecting the inner and outer layers 40 and 41 and the counter 48 securely about the foot and lower leg for resisting unwanted motion and permitting wanted motion and protecting the ankle.

The orthosis 39 can be used over an injured ankle during recovery. It can also be used inside a shoe for protecting the ankle in conjunction with the shoe. In such case, it is preferred that the shoe and orthosis be connected to one another such as by employing laces 46 as both the shoelaces and also the laces for the orthosis in the manner described with respect to orthosis 39 in FIG. 21. The inner and outer layers 40 and 41 of the orthosis can be secured to one another as by sewing for positioning and retaining the heel-sole counter 38 therein. Additional padding, not shown, could also be provided on the inside of the orthosis to aid in protecting the foot and lower leg contacted by the orthosis. A significant feature of the heel-sole counter in the shoe and orthosis of the preferred embodiment of the invention is that the lateral side of the lower portion thereof extends forward to the midfoot and upwardly to a height sufficient that in combination with the securing means or shoe with strap arrangement for maintaining the tensioned connection between the foot and shoe or orthosis, it can effectively limit or stop abduction of the calcaneocuboid, and therefore the talonavicular which acts as a unit therewith in the midtarsal joint when the subtalar joint has supinated to the position shown in FIG. 5B. This enhances control in preventing further supination or rollover thereby avoiding reducing ankle injury.

While we have shown and described several embodiments of the invention herein, it is understood that the same is not limited thereto but is suspectable to numerous changes and modifications as will be readily understood by the skilled artisan without departing from the scope of the present invention as defined in the appended claims. For example, while the preferred embodiments of the shoe, orthosis and method of the invention are specific for reducing or preventing inversion ankle injuries, the invention is also applicable for reducing or preventing eversion ankle injuries, or both inversion and eversion ankle injuries through limiting the motion of the subtalar joint by limiting the motions of segments thereof. Further, while the heel-sole counter and the heel-sole and upper of the shoe of the disclosed embodiments are formed as separate components of different materials which are integrated in the shoe at the time of manufacture, these components could be consolidated and formed of the same material as a single component. In such case, the composition of the material and/or the thickness thereof could be varied to provide the necessary structural integrity and asymmetric properties in bending for limiting excessive subtalar joint motion while permitting a normal range of motion of the ankle joint and subtalar joint. The disclosed embodiment of the shoe is specific with reference to a high-top athletic shoe, particularly a tennis shoe. However, the invention has applicability to mid-top athletic shoes, and can be used in shoes for sports other than tennis, such as for basketball shoes, football shoes, track shoes, other court shoes, running shoes and walking shoes. The invention can also be used in boots, including hiking boots, work boots, etc. The motion of the subtalar joint permitted by the invention could also be less than the full normal range of motion, such as only the "functional range" as referred to above, for example, or an amount intermediate these ranges.

Therefore, we do not wish to be limited to the details shown and described herein, but intend to cover all such changes and modifications as are encompassed by the scope and the appended claims.

We claim:

1. An athletic shoe for protecting a person's subtalar joint against inversion injury during walking, running or jumping while allowing normal ranges of motion in the ankle and subtalar joints which are for walking, running or jumping, said shoe comprising a mid- or high-top upper, a heel-sole, and said shoe including reinforcement for limiting shoe rollover and inversion ankle injury while permitting motion of the foot from a neutral position of the foot about the ankle joint in both plantarflexion and dorsiflexion in the sagittal plane during walking, running or jumping and permitting flexing motion of the foot about the joint between the forefoot and the midfoot, and said shoe further including an external strap which is non-stretchable in length and which can be adjustably tensioned over the anterior aspect of the ankle between points of attachment to the shoe on or about the lateral heel-sole of the shoe and the medial anterior aspect of the ankle, said points on or about the lateral heel-sole of the shoe including points fore and aft of the axis of the ankle joint as seen in a top plan view of the foot where two ends of said strap are attached, the intermediate portion of the external strap being free floating and adjustably secured by means of a free floating loop to the shoe at a medial, anterior and proximal aspect of the medial malleoli when said shoe is secured on the foot.

2. The shoe according to claim 1, wherein said shoe is a tennis shoe.

3. The shoe according to claim 1, wherein said reinforcement includes a heel-sole counter which is formed integrally with said upper and said heel-sole of said shoe.

4. The shoe according to claim 1, wherein said reinforcement includes a heel-sole counter which is a separate orthosis which is used inside said shoe in combination with said shoe.

5. The shoe according to claim 4, wherein means are provided for connecting said orthosis and said shoe to one another about the foot in use.

6. The shoe according to claim 1, wherein said reinforcement includes a heel-sole counter which vertically supports said external strap of said shoe when the shoe is secured on the foot.

7. The shoe according to claim 1, wherein said reinforcement includes a heel-sole counter.

8. The shoe according to claim 7, wherein said heel-sole counter is in a form to normally position the foot in the shoe in slight dorsiflexion such that when the foot planarflexes it creates tension on the heel-sole counter for assisting the foot upon its return to its starting position.

9. The shoe according to claim 7, wherein said heel-sole counter is formed of plastic.

10. The shoe according to claim 7, wherein said heel-sole counter includes a sole extension which functions as a spring for storing energy when deflected to provide assistance during the stance phase heel off portions of gait, running and jumping activities for improving athletic performance.

11. The shoe according to claim 10, wherein said heel-sole counter is integrated in said upper and said heel-sole of the shoe, said sole extension being flattened in fabrication of the shoe so that it is preloaded as a spring.

12. The shoe according to claim 7, wherein said heel-sole counter includes a flared lateral non-collapsible wedge or buttress which shifts the anatomical weight bearing line of the shoe laterally to reduce torsional stress about the subtalar joint.

13. The shoe according to claim 11, wherein said shoe includes a flared lateral non-collapsible wedge or buttress which shifts the anatomical weight bearing line of the shoe laterally to reduce torsional stress about the subtalar joint.

14. The shoe according to claim 13, wherein said shoe includes both a flared lateral non-collapsible heel wedge or buttress and a flared lateral non-collapsible sole wedge or buttress for said lateral shifting of said anatomical weight bearing line.

15. The shoe according to claim 14, wherein said heel wedge or buttress and said sole wedge or buttress are located in the vicinity of respective ones of said points of attachment of said external strap to the shoe.

16. A shoe for protecting a person's subtalar joint against inversion injury while allowing normal ranges of motion in the ankle and subtalar joints, said shoe comprising a mid- or high-top upper, a heel-sole, and said shoe including reinforcement for limiting shoe rollover and inversion ankle injury while permitting motion of the foot from a neutral position of the foot about the ankle joint in both plantar-flexion and dorsiflexion in the sagittal plane and permitting the flexing motion of the foot about the joint between the forefoot and the midfoot, and said shoe further including a strap for securing the shoe on a person's foot, wherein said strap is non-stretchable in length and can be adjustably tensioned over the anterior aspect of the ankle between points of attachment of the strap to the shoe on or about the lateral heel-sole of the shoe and the medial anterior aspect of the ankle, said points on or about the lateral heel-sole of the shoe including points fore and aft of the axis of the ankle joint as seen in a top plan view of the foot where respective, spaced apart portions of said strap are attached, the intermediate portion of the strap between said spaced apart portions being free floating and also positioned so that it can be adjustably secured to the shoe at a medial, anterior and proximal aspect of the medial malleoli when said shoe is secured on the foot.

* * * * *